United States Patent [19]
Krapcho

[11] Patent Number: 5,935,969
[45] Date of Patent: Aug. 10, 1999

[54] PYRIDO-THIOPYRANDOINAZOLES WITH ANTITUMOR ACTIVITY

[75] Inventor: A. Paul Krapcho, Shelburne, Vt.

[73] Assignee: University of Vermont, Burlington, Vt.

[21] Appl. No.: 08/973,865

[22] PCT Filed: Jul. 3, 1996

[86] PCT No.: PCT/US96/10966

§ 371 Date: Jan. 5, 1998

§ 102(e) Date: Jan. 5, 1998

[87] PCT Pub. No.: WO97/02267

PCT Pub. Date: Jan. 23, 1997

[51] Int. Cl.⁶ .................. A61K 31/435; C07D 495/12
[52] U.S. Cl. .............................. 514/287; 546/64
[58] Field of Search ................. 514/287; 546/64

[56] References Cited

U.S. PATENT DOCUMENTS

| | | | |
|---|---|---|---|
| 4,604,390 | 8/1986 | Elslager et al. | 514/222 |
| 5,519,029 | 5/1996 | Krapcho et al. | 514/287 |

Primary Examiner—Alan L. Rotman
Assistant Examiner—Charanjit S. Aulakh
Attorney, Agent, or Firm—Nikaido Marmelstein Murray & Oram, LLP

[57] ABSTRACT

This invention is directed to compounds of formula (I) wherein one of X, Y, Z or T is nitrogen (=N—) and the others are =CH—; these compounds have been shown to have antitumor activity.

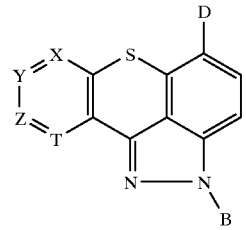

(I)

19 Claims, No Drawings

PYRIDO-THIOPYRANDOINAZOLES WITH ANTITUMOR ACTIVITY

CROSS-REFERENCE

This application is a 371 of PCT/US96/10966 filed Jul. 3, 1996 which has been published as [WO]97/02267.

BACKGROUND OF THE INVENTION

1. Field of the invention

This invention is directed to 2H-pyrido[3',2':5,6] thiopyrano[4,3,2-cd]indazoles, 2H-pyrido[4',3':5,6] thiopyrano[4,3,2-cd]indazoles, 2H-pyrido[3',4':5,6] thiopyrano[4,3,2-cd]indazoles and 2H-pyrido[2',3':5,6] thiopyrano[4,3,2-cd]indazoles substituted in the positions 2 and 5.

These compounds have been shown to have antitumor activity.

2. Background

Certain 1,4-bis[(aminoalkyl)amino]anthracene-9,10-diones have been reported which show antitumor activity in clinical trials. Of particular interest has been ametantrone, 1,4-bis[(2-(2-hydroxyethylamino)ethyl)amino]anthracene-9,10-dione and mitoxantrone, 5,8-dihydroxy-1,4-bis[(2-(2-hydroxyethylamino)ethyl)amino]anthracene-9,10-dione [Zee-Cheng et al., J Med. Chem., 21, 291–4 (1978); Cheng et al., "Progress in Medicinal Chemistry", Ellis, G. P. and West, G. B., eds.; Elsevier: Amsterdam, 1983, vol. 20, pp. 83 and references cited therein]. Mitoxantrone is a broad spectrum oncolytic agent, whose activity is similar to that of the anthracycline antibiotic doxorubicin. Clinical trials have demonstrated that mitoxantrone has particularly promising activity in the treatment of advanced breast cancer, acute leukemia and lymphoma [Legha, Drugs of Today, 20, 629 (1984)]. Although animal studies have demonstrated a diminished cardiotoxicity in comparison to doxorubicin, some clinical cardiotoxicity has been observed also with mitoxantrone, mostly in patients previously treated with doxorubicin [R. Stuart Harris et al., Lancet, 219, (1984) and references cited therein].

Ametantrone has been reported to be, in animals, about 10-fold less potent and cardiotoxic than mitoxantrone. Because a delayed toxicity is observed only with mitoxantrone after administration of the two drugs by the i.p. route to non-tumor bearing rats at equieffective antitumor dosages, it is suggested that the presence of the 5,8-dihydroxy substitution in mitoxantrone might be implicated in the delayed deaths [Corbett et al., Cancer Chemother. Pharmacol., 6, 161 (1981)].

In addition, both mitoxantrone and ametantrone have a remarkable myelodepressive toxicity and both compounds show cross-resistance to cell histotypes developing resistance against doxorubicin mediated by overexpression of glycoprotein P. Such a resistance, which is named multidrug resistance (MDR), involves a number of antitumor antibiotics, among which amsacrine and podophyllotoxinic In addition, both mitoxantrone and ametantrone have a remarkable myelodepressive toxicity and both derivatives, and it is one of the main reasons for therapeutic failures in the treatment of solid tumors with said antibiotics.

In an attempt to overcome the above mentioned drawbacks some chromophore modified anthracenediones have been prepared. For example, E. P. Patent Application 103.381 discloses 2-aminoalkyl-5-aminoalkylamino substituted anthra[1,9-cd]pyrazol6(2H)-ones (anthrapyrazoles) which are claimed to have antitumor activity. The antitumor activity of said compounds in a number of preclinical models has been reported by H. D. Hollis Showalter et al. [J. Med. Chem., 30, 121–131 (1987)]. However anthrapyrazoles are not devoid of toxic side effects, with severe leukopenia (W.H.O. grade 3 and 4) and neutropenia (W.H.O. grade 4) being dose limiting in phase I and phase II clinical trials with the anthrapyrazole CI-941 [I. E. Smith et al., J. Clin. Oncol., 9, 2141–2147 (1991)]. Moreover a marked nephrotoxicity is associated with CI-941 treatment in the rat [D. Campling and M. E. C. Robbins, Nephrotoxicity, Peter H. Dekker Bach editor, pp. 345–352 (1991), New York; see Chemical Abstract 116: 294n (1992)] and these authors suggest that renal injury may be a clinical problem with anthrapyrazole therapy. In addition recent reports [Drugs of the Future, 17, 725 (1992); Judson, I. R. et al., Proc. Amer. Assoc. Cancer Res., 32, abstr. 1059 (1991)] indicate that the anthrapyrazole CI-941 induces irreversible cardiotoxicity in humans, although no symptoms of cardiac failure or acute cardiac events have been reported.

Furthermore, WO94/06795 (31.03.94) describes azaanthrapyrazole derivatives which are endowed with antitumor activity.

In the attempt to reduce the radical formation "in vivo" by eliminating the "quinonoid" structure, benzothiopyranoindazoles have been prepared [H. D. Hollis Showalter et al., J. Med. Chem., 31, 1527–1539 (1988)]. In these compounds a carbonyl group at C-6 position has been replaced by a sulphur atom. A compound of this series, CI-958, has been chosen for development toward clinical trials.

However, the search for newer active analogues is still highly desirable. We have now discovered that the introduction of one nitrogen atom in the positions 7, 8, 9 or 10 of the above mentioned benzothiopyranoindazoles provides 2H-pyrido[3',2':5,6]thiopyrano[4,3,2-cd]indazoles, 2H-pyrido[4',3':5,6]thiopyrano[4,3,2-cd]indazoles, 2H-pyrido[3',4':5,6]thiopyrano[4,3,2-cd]indazoles and 2H-pyrido[2',3':5,6]thiopyrano[4,3,2-cd]indazoles substituted in the positions 2 and 5, which have showed a marked antitumor activity.

BRIEF SUMMARY OF THE INVENTION

The compounds of the invention have the general formula (I):

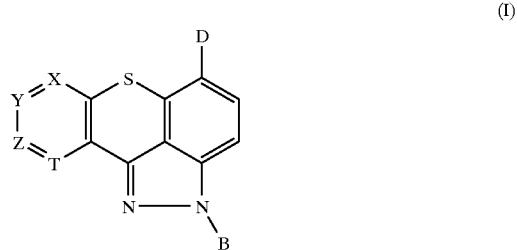

wherein:
one of X, Y, Z or T is nitrogen (=N—) and the others are a =CH— group; D is selected from the group consisting of nitro or —NH—A, wherein A is on its turn selected in the group consisting of hydrogen, —CO—CH$_2$—NR$_2$R$_3$, C$_1$–C$_{10}$ alkyl; C$_2$–C$_{10}$ alkyl having one or two substituents selected from the group consisting of OR$_1$ and —NR$_2$R$_3$; C$_2$–C$_{10}$ alkyl interrupted by one or two oxygen atoms or by one —NR$_4$—group, and said C$_2$–C$_{10}$ alkyl is optionally substituted by one or two hydroxy (OH) or —NR$_2$R$_3$ groups;

B is selected in the group consisting of $C_1$–$C_{10}$ alkyl; $C_2$–$C_{10}$ alkyl having one or two substituents selected from the group consisting of $OR_1$ and —$NR_2R_3$; $C_2$–$C_{10}$ alkyl interrupted by one or two oxygen atoms or by one —$NR_4$— group, and said $C_2$–$C_{10}$ alkyl is optionally substituted by one or two hydroxy (OH) or —$NR_2R_3$ groups;

$R_1$ is selected from the group consisting of hydrogen, $C_1$–$C_6$ alkyl, —$S(O_2)R_5$, $C_2$–$C_6$ alkyl optionally substituted by —$NR_2R_3$;

$R_2$ and $R_3$ may be the same or different and are selected from the group consisting of hydrogen, $C_1$–$C_{10}$ alkyl, $C_2$–$C_{10}$ alkyl substituted with one or two hydroxy (OH) groups, or $R_2$ and $R_3$ taken together with the nitrogen atom to which they are linked form a 5- or 6-member aromatic or non-aromatic heterocyclic ring which optionally contains another heteroatom such as sulfur, oxygen or nitrogen;

$R_4$ is selected from the group consisting of hydrogen, $C_1$–$C_{10}$ alkyl, $C_2$–$C_{10}$hydroxyalkyl, $C_2$–$C_{10}$ alkyl substituted with —$NR_2R_3$;

$R_5$ is selected from the group consisting of $C_1$–$C_{10}$ alkyl, phenyl, phenylalkyl, as free bases and their salts with pharmaceutically acceptable acids.

The present invention also concerns the tautomeric forms, the single enantiomers and diastereoisomers of the compounds of formula (I), as well as mixtures thereof.

The present invention also concerns the non-toxic salts of the compounds of formula (I) with acids acceptable for pharmaceutical and veterinary use such as those obtained by addition of inorganic acids like hydrochloric, hydrobromic, sulfuric, phosphoric, pyrophosphoric acid and/or of organic acids such as acetic, propionic, citric, benzoic, lactic, maleic, fumaric, succinic, tartaric, glutamic, aspartic, gluconic, ascorbic acids and the like.

DETAILED DESCRIPTION OF THE INVENTION

In compounds (I) the term "phenyl" means phenyl rings which can optionally contain substituents such as ($C_1$–$C_4$) alkyl groups, $CF_3$, halogen atoms, nitro, amino, acetylamino, formylamino, dimethylamino, diethylamino, hydroxy, methoxy and ethoxy groups.

Preferred examples of $C_1$–$C_{10}$ alkyl groups are methyl, ethyl, n-propyl, sec-propyl, n-butyl, sec-butyl, tert-butyl, n-pentyl, n-hexyl.

Preferred examples of phenylalkyl is 4-methylphenyl. When in compounds of formula (I) A and B are a $C_2$–$C_{10}$ alkyl interrupted by one or two oxygen atoms or by one —$NR_4$— group and optionally substituted by one or two hydroxy or —$NR_2R_3$ groups, at least two carbon atoms are preferably interposed between said oxygen atoms and/or the —$NR_4$— and —$NR_2R_3$ groups.

When in compounds of formula (I) the —$NR_2R_3$ substituent is a 5–6 member aromatic or not aromatic heterocyclic ring which may contain another heteroatom such as sulfur, oxygen and nitrogen, preferred examples of said heterocyclic rings are 1-imidazolyl, 4-hydroxy-1-imidazolyl, 2-imino-1(3H)imidazolyl, 1-pyrrolyl, 1-tetrahydropyrrolyl, 1-pyrazolyl, 4-morpholinyl, 1-piperidinyl, 1-piperazinyl, 1-(4-methyl)piperazinyl, 1-(4-benzyl)piperazinyl.

The compounds of formula (I) are those depicted in table 1, wherein D and B are as above defined.

TABLE 1

| X | Y | Z | T | structure | name of the heterocyclic system |
|---|---|---|---|-----------|-------------------------------|
| CH | CH | CH | N | 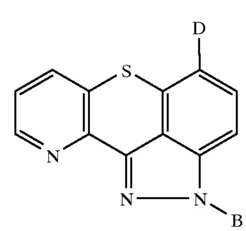 | 2H-pyrido[2',3':5,6]thiopyrano[4,3,2-cd]indazole |

TABLE 1-continued (I)

| X | Y | Z | T | structure | name of the heterocyclic system |
|---|---|---|---|-----------|-------------------------------|
| CH | CH | N | CH | | 2H-pyrido[3',4':5,6]thiopyrano[4,3,2-cd]indazole |
| CH | N | CH | CH | | 2H-pyrido[4',3':5,6]thiopyrano[4,3,2-cd]indazole |
| N | CH | CH | CH | 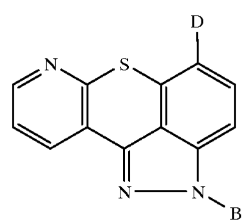 | 2H-pyrido[3',2':5,6]thiopyrano[4,3,2-cd]indazole |

Preferred compounds are those according to formula (I) wherein X, Y, Z and T are as above defined, D is a —NH—A group and A and B are independently selected from the group consisting of:

- residue of formula —(CH$_2$)$_p$—NH$_2$ wherein p is the integer 2 or 3;
- residue of formula —(CH$_2$)$_p$—NR$_2$R$_3$ wherein p is as above defined and both R$_2$ and R$_3$ are methyl or ethyl or 2-hydroxyethyl;
- residue of formula —(CH$_2$)$_p$—NR$_2$R$_3$ wherein p is above defined and R$_2$ is hydrogen and R$_3$ is methyl;
- residue of formula —(CH$_2$)$_p$—NR$_2$R$_3$ wherein p is above defined and —NR$_2$R$_3$ is 4-morpholinyl, 1-piperidinyl, 1-piperazinyl, 1-imidazolyl;
- residue of formula —(CH$_2$)$_p$—OH wherein p is as above defined;
- residue of formula —(CH$_2$)$_p$—NH—(CH$_2$)$_q$—OH wherein p and q are independently an integer selected from the group consisting of 2 or 3.

Other preferred compounds are those in which D is selected in the group consisting of nitro, amino and —NHCO—CH$_2$—NH$_2$ and B is as just above defined. Particularly preferred compounds of formula (I) are those in which A and B are as previously defined and X or Z are nitrogen.

Even more particularly preferred compounds are those in which X or Z are nitrogen, D is a —NH—A group and A and B are independently a residue of formula —(CH$_2$)$_p$—NR$_2$R$_3$, wherein p is as above defined and both R$_2$ and R$_3$ are methyl or ethyl or 2-hydroxyethyl.

The compounds of formula (I) can be prepared by the reaction of a compound of formula (III):

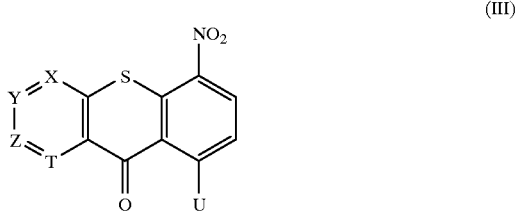

(III)

wherein X, Y, Z and T are as above defined and U is selected from the group consisting of F or Cl, with a hydrazine of formula (IV):

$$H_2N-NH-B'\qquad(IV)$$

wherein B' has the same meanings as B is defined in formula (I), or B' is a group that can be converted into B by removal of protective groups for the primary or secondary amines and hydroxy groups optionally present in B', to give compound of formula (II):

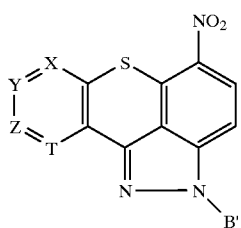

(II)

in which X, Y, Z, T and B' are as above defined.

The removal of protecting groups optionally present gives the compounds of formula (I) in which D is a nitro group.

Alternatively, said intermediate (II) is subjected to reduction of the nitro group to give the intermediate of formula (IIa):

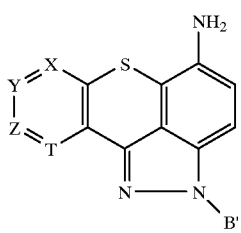

(IIa)

which is then converted into the compounds of formula (I) in which D is an amino group by removal of the protecting groups optionally present.

Alternatively, the intermediate (IIa) is converted into the compounds of formula (I) in which D is a —NH—A group and A has the meanings above defined, with the exception of hydrogen and —CO—CH$_2$—NR$_2$R$_3$, by condensation of the amino group with a reactant of formula (V):

L—A'  (V)

in which A' has the same meanings as A is defined in formula (I) or A' is a group that can be converted into A by removal of protective groups for the primary or secondary amines or hydroxy groups optionally present in A' and L is an atom selected in the group of chlorine, bromine and iodine or is a -O-Tosyl group, and subsequent removal of protective groups optionally present on the side chains A' and B'.

Alternatively, A' is a group of formula —CO—A'', in which on its turn A'' is selected in the group consisting of C$_1$–C$_9$ alkyl; C$_1$–C$_9$ alkyl having one or two substituents selected from the group consisting of OR$_1$ and —NR$_2$R$_3$; C$_1$–C$_9$ alkyl interrupted by one or two oxygen atoms or by one —NR$_4$— group, and said C$_1$–C$_9$ alkyl is optionally substituted by one or two hydroxy (OH) or —NR$_2$R$_3$ groups, and in which the hydroxy or the amine group can optionally be protected with conventional protective groups. In this case, L is a OH group, a halogen atom (chlorine, bromine or iodine) or a suitable leaving group well known to the skilled artisan. Such a reaction, followed by the removal of the protecting groups optionally present, gives the compounds of formula (I) in which A is a —CO—CH$_2$—NR$_2$R$_3$ group. They on their turn give the other compounds of formula (I) by reduction of the amidic moiety to amine.

Protective groups for the primary and/or secondary amines optionally present in A' and/or B' which can advantageously be used for the preparation of compounds of formula (I) are represented by (C$_1$–C$_3$)acyl derivatives (preferably acetyl derivatives), (C$_1$–C$_4$)alkoxycarbonyl derivatives (preferably tert-butoxycarbonyl derivatives) and by (C$_7$–C$_{10}$)aralkyloxycarbonyl derivatives (preferably benzyloxycarbonyl derivatives).

The reaction of compounds (III) with the hydrazines (IV) can be performed by reacting compounds (III) with a stoichiometric amount of hydrazines (IV) or an excess of hydrazines (IV). The reaction is usually performed in an inert solvent such as methylene chloride, chloroform, 1,1,1-trichloroethane, dimethoxyethane, tetrahydrofuran, dimethylsulfoxide, dimethylformamide, pyridine, picoline and mixtures thereof, or if it is desired, using compound (IV) itself as the solvent, optionally in the presence of an inorganic base such as an alkaline or alkaline-earth carbonate or hydrogen carbonate or an organic base such as a trialkylamine, at a temperature from –20° C. to the reflux temperature of the solvent. Preferably, the reaction is carried out in a solvent such as dimethylformamide, pyridine, tetrahydrofuran, dimethylsulfoxide or N,N,N',N'-tetramethylethylenediamine, using 1 to 10 equivalents of compound (IV) for 1 equivalent of compound (III) and working at a temperature ranging from 5° C. to 50° C.

If necessary, the removal of the protective group for the primary and/or secondary amino functions is carried out following the procedures well known to those skilled in the art. Useful teachings can be found in Green, T. W., Wuts, P. G. M., "Protective Groups in Organic Synthesis", second Edition, John Wiley & Sons, 1991.

For example, the removal of the N-(tert-butoxycarbonyl) protective group can be performed by treatment of the compound with an excess of anhydrous or aqueous hydrochloric acid in a solvent such as a (C$_1$–C$_4$)alkanol, dichloromethane, chloroform or mixtures thereof, at a temperature of 0° C. to the reflux temperature of the solvent and for a time ranging from several minutes to a few hours. Preferably the reaction is performed in ethanol or in chloroform using from 10 to 20 molar equivalents of anhydrous hydrochloric acid at a temperature of from 20° C. to 50° C., and is generally complete in four hours. The reaction of reduction of the nitro group of compounds (II) to give compounds (IIa) is performed by catalytic hydrogenation, treating in hydrogen atmosphere a compound (II), in a suitable solvent such as glacial acetic acid, an alkanol such as methanol or ethanol, an ether such as 1,4-dioxane, tetrahydrofuran or a solvent such as methylene chloride or chloroform, in the presence of catalytic amounts (from 0.1 to 0.3 equivalents) of a catalyst such as 10% palladium on carbon, Nickel Raney or 10% platinum on carbon and at a pressure of from atmospheric pressure to 100 psi.

Preferably, the reaction is carried out in glacial acetic acid, using 10% palladium on carbon as a catalyst and at a pressure of about 70 psi.

Alternatively, the reduction of the nitro group of compounds (II) to give compounds (IIa) may be performed following other methods known in the art, such as the use of FeSO$_4$ in basic conditions (ammonia or sodium hydroxide) or the use of metals or salts thereof, optionally in acidic conditions. Suitable examples of such reducing agents are SnCl$_2$, SnCl$_2$ in the presence of hydrochloric acid or Zn in the presence of hydrochloric acid.

The alkylation of intermediates (IIa) with intermediates of formula L-A' to give the compounds of formula (I) is performed by reacting the intermediate (IIa) with a molar excess of the reactant of formula (V) in an inert solvent such as benzene, toluene, chlorobenzene and the like, or an alcohol such as isopropanol or in a nitrile such as acetonitrile, and in the presence of an inorganic base such as an alkaline or alkaline-earth carbonate or hydrogencarbonate or an organic base such as trialkylamine. Preferably, the reaction is carried out in an aromatic solvent such as toluene, in the presence of potassium carbonate and at a temperature ranging from room temperature to the reflux temperature of the solvent.

The acylation reaction of intermediates (IIa) with compounds of formula L—CO—A" is usually performed, when L is a OH group, in the presence of a condensing agent such as dicyclohexylcarbodiimide and the like, at a temperature ranging from −10° C. to room temperature and in an inert solvent such as an ether (tetrahydrofuran, diethyl ether and the like).

The reduction of amidic moiety into amine can be preferentially performed in an inert solvent such as toluene or benzene, at a temperature ranging from room temperature to the reflux temperature of the solvent and in the presence of a reducing agent such as Red-Al, LiAlH$_4$ or other suitable hydrides. The intermediates (III) can be prepared by cyclization of the compounds of formula (VI):

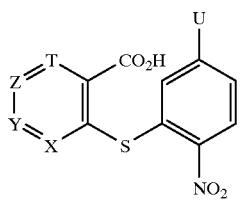

(VI)

in which X, Y, Z, T and U are as above defined.

Said reaction can be performed using different methods known in the art, such as for example:

i) transforming the carboxylic acid moiety into an acyl chloride by reaction with thionyl chloride, for example, and subsequently performing a Friedel-Craft reaction in the presence of a Lewis acid such as alluminum trichloride, in a suitable solvent such nitrobenzene and at a temperature ranging from −10° C. to 50° C.;

ii) cyclizing the compounds (VI) in the presence of fuming sulfuric acid (10–30% sulfur trioxide), at a temperature ranging from room temperature to 150° C.;

iii) cyclizing the compounds (VI) in the presence of polyphosphoric acid silyl ester (PPSE) and of phosphorus pentoxide, at a temperature ranging from 50° C. to 210° C.

The compounds of formula (VI) can be obtained starting from the compounds of formula (VIII):

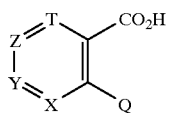

(VIII)

in which X, Y, Z and T are as above defined and Q is a chlorine atom or a diazo group —N$_2^+$Cl$^-$, by reaction with a compound of formula (VII):

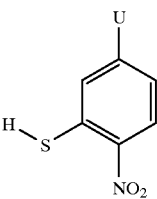

(VII)

in which U is as above defined.

When X or Z are nitrogen, then Q is preferentially chlorine; when Y or T are nitrogen, Q is preferentially a —N$_2^+$Cl$^-$ group.

When Q is chlorine, the reaction is preferentially performed in a suitable solvent such as a ketone (acetone, methyl ethyl ketone and the like) and at a temperature ranging from room temperature to the boiling point of the solvent.

When Q is a —N$_2^+$Cl$^-$ group, the compounds (VIII) are prepared "in situ", following the methods known in the art, by reaction of the amine derivatives (IX):

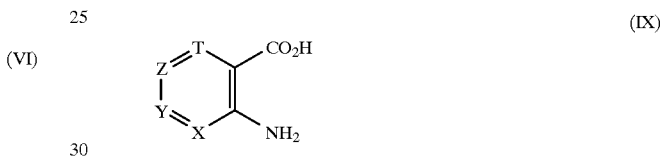

(IX)

with sodium nitrite in the presence of hydrochloric acid at a temperature ranging from −10° C. to 10° C. The compounds (VIII) so prepared are then reacted without isolation with the compounds (VII) at a temperature ranging from 0° C. to 70° C., obtaining the compounds of formula (VI).

Alternatively, compounds (VIII) in which Q is a —N$_2^+$Cl$^-$ can be reacted without isolation with equimolar amounts of O-ethylxanthic acid, potassium salt. The resulting intermediates give compounds (VI) by treatment with sodium ethoxide in ethanol and subsequently with 2,4-dichloronitrobenzene.

The compounds of formula (VIII) when Q is a chlorine atom or the compounds of formula (IX) are commercial product or can be prepared starting from commercial product following methods known in the art, such as for example those described in:

Ross, W. C. J., J.C.S., C, 1816–21 (1966): synthesis of 4-chloro nicotinic acid;

Winn, M. et al., *J. Med. Chem.*, 36, 2676–88 (1993);

Fibel, C. R. et al., J.A.C.S., 70, 3908 (1948): synthesis of 3-amino isonicotinic acid.

BIOLOGICAL EVALUATION OF THE COMPOUNDS OF THE INVENTION

The evaluation of the biological activity for the compounds of this invention was performed "in vitro" and "in vivo" following the protocols developed by the U.S. National Cancer Institute.

The evaluation of the "in vitro" cytotoxic activity of the compounds of the invention was performed using the following cell lines: a murine sarcoma (S-180) and its subline expressing multidrug resistance (S-180/A-10), a leukemia (L1210), a human colon adenocarcinoma cell line (LoVo) isolated from a metastatic nodule and its subline expressing multidrug resistance. This latter subline is resistant to a number of antitumor agents, among which are doxorubicin, VP-16 and vincristine. This subline (named LoVo/DX) shows reduced accumulation of doxorubicin and overexpression of a protein (Grandi, M., Geroni, C., Giuliani, F. C., British J. Cancer, (1986), 54, 515). The compounds were tested according to the MTT assay (Mosman, T. "Rapid Colorimetric Assay for Cellular Growth and Survival: Application to Proliferation and Cytotoxicity Assay", J. Immunol. Methods, (1983), 65, 55–63; Green, L. M., "Rapid Colorimetric Assay for Cell Viability; Application to the Quantitation of Cytotoxic and Growth Inhibitory Lymphokines", J. Immunol. Methods, (1984), 70, 257–268) in comparison with mitoxantrone and doxorubicin.

The pharmacological data for some representative compounds of the present invention are reported in Tables II and Ill. A comparison with the prior art compound C1941 and with doxorubicin and mitoxantrone is also provided in Table II. The columns headed L1210, S180 LoVo and LoVo/Dx contain the $IC_{50}$ values against said tumor cell lines, as above described.

In general, representative compounds of this invention exhibited a high cytotoxicity in all the cell lines tested. When mitoxantrone was tested in the LoVo/DX cell line, a resistance index RI (defined as the ratio of the $IC_{50}$ for the resistance cell line to the $IC_{50}$ for the sensitive cell line) as high as 22.5 was found, showing that this subline does have an acquired resistance to mitoxantrone. On the other hand, representative compounds of this invention, when tested in the same resistant subline, show no cross resistance with mitoxantrone. The "in vitro" evaluation of representative compounds of this invention suggests that they are able to retain a high activity also in the resistant cell line, while the prior art compound CI-941 loses completely its activity. Studies of the biological activity "in vivo" of representative compounds of the invention were performed using the P388 murine leukemia model. P388 murine leukemia cells were intravenously (iv) injected in CD2F1 mice. Treatment was initiated approximately 24 hours after tumor transplantation and dosages of the drug were administered iv (P388 iv/iv) according to preestablished protocols, usually at 3-day intervals. The studies were done over a 60-day period and the date of death for each animal was recorded. The % T/C was determined using the mean survival time (MST) for each group according to the formula % $T/C=[(MST \text{ treated})/(MST \text{ control})] \times 100$ Representative compounds of this invention were able to increase the survival time of treated animals, leading to high % T/C values at well tolerated dosages. Since representative compounds of this invention show good results against this significant "in vivo" model of murine P388 leukemia, which is considered to be predictive of antitumor activity in humans, the compounds disclosed herein are expected to be operative against human leukemias and solid tumors sensitive to treatment with antitumor antibiotics.

The compounds of the invention may therefore be used as active ingredients of therapeutic compositions to induce regression and/or palliation of cancers in mammals when administered in amounts ranging from about 1 mg to about 0.4 g per kilogram of body weight. A preferred dosage regimen would be from about 1 mg to about 50 mg per kilogram of body weight per day. Unit dosage may be employed so that from about 70 mg to about 3.5 g of the active compound for a subject of about 70 kg of body weight are administered in a 24-hour period. The dosage may be adjusted to be compatible to other treatment regimens, such as radiation therapy.

The pharmaceutical composition may be in the form of tablets, capsules, gel capsules, suppositories, lyophilized powders and solutions for intravenous administration.

The invention is illustrated by the following non-limiting examples and variations which are readily apparent to those skilled in the art.

EXPERIMENTAL PART

Preparation 1

2-(2-nitro-5-chloro)thiophenoxynicotinic acid (compound (VI): X=N)

A solution of 2-nitro-5-chlorobenzenethiol (0.26 9) in acetone (2 ml) was added to 2-chloronicotinic acid (0.11 g). The suspension was refluxed for 5 hrs and the resultant mixture was cooled to room temperature. The bright yellow precipitate was collected by filtration, washed with acetone to yield a yellow solid (0.12 g), m.p. 248–249° C.

$^1$H NMR in d6-DMSO 8.39 ppm (dd, J=1.7 Hz, 4.7 Hz, 1H); 8.27 ppm (dd, J=1.7 Hz, 7.9 Hz, 1H); 8.10 ppm (d, J=8.7 Hz, 1H); 7,85 ppm (d, J=2.3 Hz, 1H 7.76 ppm (dd, J=2.3 Hz, 8.7 Hz, 1H); 7.30 ppm (dd, J=4.7 Hz, 7.7 Hz, 1H). Anal. Calcd. for $C_{12}H_7CIN_2O_4S$: C 46.39, H 2.27, N 9.01. Found: C 46.39, H 2.27, N 8.80.

Preparation 2

6-chloro-9-nitro-5H-[1]benzothiorpyrano[2,3:]pyridin-5-one (compound (III). X=N)

Route 1 (with fuming sulfuric acid)

0.645 g of 2-(2-nitro-5-chloro)thiophenoxynicotinic acid were added to 2 ml of fuming sulfuric acid (18–24% sulfur trioxide) and the mixture was placed in an oil bath preheated to 75° C. The solution was heated at 125–130° C. for 1.25 hrs. The mixture was removed from the oil bath, cooled to room temperature and poured over ice water (150 ml). The yellow precipitate was collected by filtration, washed with water and dried, to give 0.60 g of a solid. This material was dissolved in dimethyl formamide (DMF, 11 ml) which on cooling immediately led to a yellow crystalline fluffy solid. This solid was collected by filtration and washed with diethyl ether to remove residual DMF, yielding 0.54 g of product, m.p. 267–270° C.

$^1$H NMR in $CDCl_3$ 8.84 ppm (dd, J=1.77 Hz, J=4.60 Hz, 1H); 8.60 ppm (dd, J==1.77 Hz, J=8.05 Hz, 1H); 8.51 ppm (d, J=8.80 Hz, 1H); 7.68 ppm (d, J=8.80 Hz, 1H); 7.51 ppm (dd, J=4.6 Hz, J=8.00 Hz, 1H).

Route 2 (with thionyl chloride/ alluminum trichloride)

A mixture of 2-(2-nitro-5-chloro)thiophenoxynicotinic acid (5 g), toluene (27 ml) and thionyl chloride (6 ml) was heated at reflux for 1.5 hrs. Upon cooling, the acid chloride separated as yellow needles. The resultant mixture was concentrated to dryness by distillation and a yellow crystalline solid remained. Nitrobenzene (25 ml) for 0.5 the suspension was cooled in an ice bath for 0.5 hrs. Alluminum chloride (2 g) was slowly added while keeping the temperature below 35° C. The mixture darkened and it was stirred at room temperature for 20 hrs. The dark black suspension was poured into ice water (130 ml) and the mixture was stirred for 1 hr. The aqueous layer was removed by decantation, methanol (100 ml) was added to the nitrobenzene and the resultant solid was collected by filtration. Addition of methanol (200 ml) to the filtrate led to additional product, total weight 3.1 g. For purification, the crude material was recrystallized from ethylene glycol monoethyl ether to yield a yellow fluffy solid, m.p. 265–270 C., identical in its $^1$H—NMR spectrum to the product obtained following route 1.

Route 3 (with polyphosphoric acid silyl ester, PPSE)

A mixture of PPSE (2 g) and phosphorus pentoxide (0.25 9) was heated in an oil bath to 210° C. 2-(2-nitro-5-chloro) thiophenoxynicotinic acid (0.10 g) was added to the hot mixture and the mixture was held at this temperature for 20 minutes. The hot mixture was quenched into cold hydrochloric acid 6 N (6 ml) and the resultant mixture was allowed to stand overnight. After neutralization with sodium hydroxide, the solid was collected by filtration and dried to give 0.085 g of a solid. The crude material was heated in ethyl acetate and filtered while hot to remove some brownish insoluble material. Removal of the solvent led to product (0.045 9) identical to that prepared following routes 1 and 2.

Preparation 3
3-(2-nitro-5-chlorothiophenoxy)isonicotinic acid (compound (VI). Y=N)

A solution of 3-amino-4-carboxypyridine (1.4 g), sodium nitrite (0.81 g) and aqueous sodium hydroxide 2.9 M (13.3 ml) was added to a solution of aqueous hydrochloric acid 4.3 M (9.8 ml) while the temperature was maintained at 0–5 C. The mixture was stirred for 10 minutes and then added dropwise over the course of 2 hrs to a stirred mixture of 5-chloro-2-nitrothiophenol (2.34 g) and sodium hydroxide (2.63 g) in water (21 ml) maintained at about 53° C. (a brisk nitrogen evolution occurred). The mixture was stirred for 15 minutes, cooled to room temperature and filtered. The fitrate was made strongly acidic (pH=2) with hydrochloric acid 12 M and the precipitated solid was collected by filtration and dried to yield a brownish-orange solid (3 g). The solid was washed with dichloromethane:acetonitrile (30 ml) and dried to leave crude product (1.2 g). Crystallization from ethyl cellosolve led to the pure product, m.p. 280–281, °C.

$^1$H NMR in d6-DMSO 8.77 ppm (d, J=4.8 Hz, 1H); 8.67 ppm (s, 1H), 8.23 ppm (d, J=8.8 Hz, 1H); 7.77 ppm (d, J=4.8 Hz, 1H); 7.56 ppm (dd, J=8.8 Hz, J=2.2 Hz, 1H); 6.99 ppm (d, J=2.1 Hz, 1H).

Preparation 4
6-chloro-9-nitro-5H-[1 ]benzothionpyrano[2,3-c]pyridin-5-one (compound (III), Y=N)

A mixture of the compound of the preparation 3 (0.45 9) and thionyl chloride (2.5 ml) was heated at reflux for 1.5 hrs. The mixture changed to a dark reddish coloration. The mixture was concentrated to dryness by distillation to yield a dark red amber solid. Nitrobenzene (3.5 ml) was added and the suspension was cooled in an ice bath for 0.5 hrs. Alluminum chloride (1.02 g) was added slowly and the dark mixture was allowed to warm to room temperature and then stirred at 80–90 C. for 15 hrs. The dark suspension was poured over crushed ice (25 ml) and the mixture was stirred for 1 hr. The aqueous layer was decanted and methanol (25 ml) was added to the nitrobenzene layer. The resultant solid was collected by filtration to yield crude product (300 mg) as a dark grey solid. The solid was boiled with chloroform (75 ml) and filtered to remove some insoluble material. Concentration of the filtrate led to the pure product (75 mg).

$^1$H NMR in CDCl$_3$ 9.02 ppm (s, 1H); 8.79 ppm (d, J=5.2 Hz, 1H); 8.54 ppm (d, J=8.8 Hz, 1H); 8.09 ppm (d, J=5.2 Hz, 1H); 7.70 ppm (d, J=8.8 Hz, 1H).

Preparation 5
4-(2-nitro-5-chloro)thiophenoxy nicotinic acid (compound (VI). Z=N)

A solution of 2-nitro-5-chlorothiophenol (1.09 g) in acetone (12 ml) was added to 4-chloronicotinic acid (0.85 g). The yellow coloration of the thiol quickly disappeared and the mixture was refluxed for 1 hr. Upon cooling to room temperature, the product was filtered and washed with acetone to yield the title compound as pale yellow solid (1.72 g), m.p. 228–229° C.

$^1$H NMR in d6-DMSO 9.05 ppm (s, 1H); 8.50 ppm (d, J=5.9 Hz, 1H); 8.23 ppm (d, J=8.7 Hz, 1H); 7.98 ppm (d, J=2 Hz, 1H); 7.92 ppm (dd, J=8.7 Hz, J=2.2 Hz, 1H); 6.98 ppm (d, J=5.9 Hz, 1H).

Preparation 6
6-nitro-9-chloro-10H-[1]benzothiopyrano[2.3-c]pyridin-10-one (compound (III), Z=N)

Thiophenoxynicotinic acid (0.50 g, preparation 5) was added to fuming sulfuric acid (18–24% sulfur trioxide, 3 ml) and the mixture was placed in an oil bath which was preheated to 40° C. The dark reddish amber solution was heated to 60° C. during 10 minutes and kept at this temperature for 20 minutes. The cooled mixture was poured over ice-water (25 ml) and neutralized with solid sodium bicarbonate. The resultant bright yellow solid was collected by filtration and dried, obtaining 0.38 g of crude product. The solid was boiled in chloroform (40 ml) and filtered to remove some starting material. Concentration of the filtrate led to the pure product (0.33 g), m.p. 220–222° C.

$^1$H NMR in CDCl$_3$ 9.43 ppm (s, 1H); 8.74 ppm (d, J=5.5 Hz, 1H); 8.50 ppm (d, J=8.8 Hz, 1H); 7.70 ppm (d, J=8.8 Hz, 1H); 7.51 ppm (d, J=5.5 Hz, 1H).

Preparation 7
N'-[2-(2-dimethylamino)ethyl]-5-(2'-(N-tertbutoxycarbonyl)amino acetylamino)-2H-pyrido[3'2':5.6]thiopyrano[4,3,2-cd]indazole Dicyclohexylcarbodiimide (210 mg) was slowly added to a magnetically stirred solution of N,N-dimethyl-5-amino-2H-pyrido[3',2':5,6]thiopyrano[4,3,2-cd]indazole-2-ethanamine (300 mg) of example 2 and N-BOC-glycine (168 mg) in dry tetrahydrofuran (8 ml) at 0° C. The mixture was stirred at 0–5° C. for 20 hr and the cyclohexylurea which precipitated was removed by filtration. The filtrate was refrigerated overnight and additional urea was removed by filtration. The filtrate was concentrated to dryness by rotary evaporation and the brownish red solid was collected (434 mg). This material was recrystallized from acetonitrile/chloroform 4:1 to give the product as a yellow solid (240 mg). Purification was best accomplished by column chromatography over silica gel using gradient elution by ethyl acetate: methanol as eluent, commencing with 5:1 and gradually changing to 1:1. Removal of the eluents led to the purified product (120 mg, m.p. 173–175 ° C.).

$^1$H—NMR in CDCl$_3$ 8.34 ppm (dd, J=1.7 Hz, 4.7 Hz, 1H); 8.23 ppm (dd, J=1.7 Hz, 7.8 Hz, 1H); 7.60 ppm (broad s, 1H); 7.49 ppm (d, J=8.7 Hz, 1H); 7.15 ppm (m, J=4.7, 7.8 Hz, 1H); 6.97 ppm (d, J=8.8 Hz, 1H); 5.21 ppm (broad d, 1H); 4.39 ppm (t, J=6.9 Hz, 2H); 4.00 ppm (d, J=6.0 Hz, 2H); 2.82 ppm (t, J=8.9 Hz, 2H); 2.33 ppm (s, 6H); 1.49 ppm (s, 9H).

Preparation 8
N'-[2-(2-dimethylamino)ethyl]-5-(2'-(N-tertbutoxycarbonyl)amino acetylamino)-2H-pyrido[3',4':5,6]thipyrano[4,3,2-cd]indazole According to the procedure described in preparation 7, the title compound was prepared.

$^1$H-NMR in CDCl$_3$ 9.17 ppm (s, 1H); 8.31 ppm (d, J=5.4 Hz, 1H); 7.70 ppm (broad s, 1H); 7.40 ppm (d, J=8.8 Hz, 1H); 7.73 ppm (d, J=5.4 Hz, I H); 7.00 ppm (d, J=8.8 Hz, 1H); 5.21 ppm (broad s, 1H); 4.40 ppm (t, J=6.9 Hz, 2H); 3.99 ppm (d, J=6.0 Hz, 2H); 2.84 ppm (t, J=6.9 Hz, 2H); 2.33 ppm (s, 6H); 1.48 ppm (s, 9H).

EXAMPLE 1

N,N-dimethyl-5-nitro-2H-pyrido[3',2':5.6]thiopyrano[4,3,2-cd[indazole-2-ethanamine (X=N)

A suspension of 6-chloro-9-nitro-5H-[1]benzothiopyrano[2,3: b]pyridine-5-one (2.5 g) in DMF (25 ml) under a nitrogen blanket was cooled in an ice bath and N-(2-dimethylaminoethyl) hydrazine (1 g) was added dropwise. The coloration changed from yellow to bright orange. The suspension was stirred for 15 hrs at room temperature and the mixture was quenched over ice-water. The pH was adjusted to 10.5–11 by addition of a saturated solution of potassium carbonate. The resultant mixture was extracted with chloroform (2×100 ml) and the chloroform layer was washed with cold water (150 ml) and then with brine (2×150 ml). The chloroform was dried over magnesium sulfate, the drying agent removed by filtration and the filtrate concentrated to yield the product as a golden brown solid (2.5 g). This material crystallized readily from acetonitrile, m.p. 173–174° C.

$^1$H NMR in CDCl$_3$ 8.55 ppm (dd, J=1.4 Hz, J=4.6 Hz, 1H); 8.41 ppm (dd, J=1.4 Hz, J=7.9 Hz, 1H); 8.23 ppm (d, J=9.2 Hz, 1H); 7.33 ppm (dd, J=4.6 Hz, J=7.8 Hz, 1H); 7.05 ppm (d, J=9.2 Hz, 1H); 4.48 ppm (t, J=6.6 Hz, 2H); 2.88 ppm (t, J=6.6 Hz, 2H); 2.30 ppm (s, 6H).

EXAMPLE 2

N,N-dimethyl-5-amino-2H-pyrido[3', 2':5,6]thiopyrano[4,3,2-cd]indazole-2-ethanamine (X=N)

A mixture of the nitro analogue of example 1 (2.12 g) and 10% palladium/C (0.35 g) in glacial acetic acid (38 ml) was placed in a Parr bomb and hydrogenated for 18 hrs at about 100 psi. The mixture was filtered through celite and concentrated to yield a dark amber oil which was dissolved in chloroform (200 ml). This solution was washed with 5% aqueous ammonium hydroxide (200 ml), water (200 ml) and brine (2×200 ml). The chloroform layer was dried over sodium sulfate, the drying agent removed by filtration and the filtrate concentrated to yield the product as a bright reddish-yellow solid (1.7 g). This was crystallized from acetonitrile to yield pure product (1.1 g), m.p. 184–186° C.

$^1$H NMR in CDCl$_3$ 8.28 ppm (dd, J=1.6 Hz, J=4.7 Hz, 1H); 8.16 ppm (dd, J=1,6 Hz, J=7.8 Hz, 1H); 7.10 ppm (dd, J=4.7 Hz, J=7.8 Hz, 1H); 6.86 ppm (d, J=8.6 Hz, 1H); 6.78 ppm (d, J=8.6 Hz, 1H); 4.35 ppm (t, J=7.1 Hz, 2H); 3.39 ppm (s, 2H); 2.81 ppm (t, 7.1 Hz, 2H); 2.24 ppm (s, 6H).

Analogously, starting from the appropriate intermediate (example 3) the following compound was prepared (Y=N):

N,N-dimethyl-5-amino-2H-pyrido[4',3':5,6]thiopyrano[4,3,2-cd]indazole-2-ethanamine, $^1$H NMR in CDCl$_3$ 8.46 ppm (s, 1H); 8.34 ppm (d, J=5.2 Hz, 1H); 7.76 ppm (d, J=5.2 Hz, 1H); 6.88 ppm (d, J=6.5 Hz, 1H); 6.80 ppm (d, J=8.7 Hz, 1H); 4.37 ppm (t, 2H); 3.38 ppm (br s, 2H); 2.83 ppm (t, 2H); 2.31 ppm (s, 6H).

EXAMPLE 3

N,N-dimethyl-5-nitro-2H-pyrido[4',3':5,6]thiopyrano[4,3,2-cd]indazole-2-ethanamine (Y=N)

A suspension of the compound of preparation 4 (0.10 g) in DMF (0.8 ml) under a nitrogen blanket was cooled in an ice bath and N-(2-dimethylaminoethyl)hydrazine (0.043 g) was added dropwise. The colour changed to bright orange and the suspension was allowed to stir at room temperature for 12 hrs. The mixture was quenched over ice water and basified with aqueous sodium bicarbonate. The resultant solid was collected by filtration and dried to yield the pure product (0.0359), m.p. 205–206° C. $^1$H NMR in CDCl$_3$ 8.83 ppm (s, 1H); 8.59 ppm (d, J=5.2 Hz, 1H); 8.30 ppm (d, J=9.3 Hz, 1H); 8.10 ppm (d, J=5.1 Hz, 1H); 7.11 ppm (d, J=9.2 Hz, 1H); 4.52 ppm (t, J=6.5 Hz, 2H); 2.90 ppm (t, J=6.5 Hz, 2H); 2.31 ppm (s, 6H).

EXAMPLE 4

N,N-dimethyl-5-nitro-2H-pyrido[3',4':5,6]thiopyranol[4,3,2cd]indazole-2-ethanamine (Z=N)

N-(2-dimethylaminoethyl)hydrazine (25 mg) was added to a suspension of the compound of preparation 6 (60 mg) in DMF (0.5 ml). The resultant orange suspension was allowed to stir for 15 hrs at room temperature. The mixture was added to cold water (5 ml) and treated with aqueous sodium bicarbonate. The orange solid was collected by filtration, washed thoroughly with water and dried to yield 57 mg of the product. The sample was recrystallized from acetonitrile. m.p. 214–215° C.

$^1$H NMR in CDCl$_3$ 9.40 ppm (s, 1H); 8.52 ppm (d, J=5.5 Hz, 1H); 8.27 ppm (d, J=9.3 Hz, 1H); 7.46 ppm (d, J=5.6 Hz, 1H); 7.12 ppm (d, J=9.3 Hz, 1H); 4.51 ppm (t, J=6.5 Hz, 2H); 2.91 ppm (t, J=6.5 Hz, 2H); 2.27 ppm (s, 6H).

EXAMPLE 5

N,N-dimethyl-5-amino-2H-pyrido[3',4':5,6]thiopyrano[4,3,2-cd]indazole-2-ethanamine (Z=N)

A mixture of the compound of example 4 (0.25 g) and 10% palladium/C (0.042 g) in glacial acetic acid (4.5 ml) was placed in a Parr bomb and hydrogenated for 18 hrs at about 70 psi pressure. The mixture was concentrated to dryness, diluted with 5% aqueous ammonium hydroxide:chloroform (1:1) and then filtered over celite. The chloroform layer was separated from the filtrate and washed with water and brine. The chloroform was removed by rotary evaporation to yield the product (0.15 g).

$^1$H NMR in CDCl$_3$ 9.10 ppm (s, 1H); 8.25 ppm (d, J=5.4 Hz, 1H); 7.12 ppm (d, J=5.4 Hz, 1H); 6.88 ppm (d, J=8.7 Hz, 1H); 6.78 ppm (d, J=8.7 Hz, 1H); 4.35 ppm (t, J=7.0 Hz, 2H); 3.34 ppm (br s, 2H); 2.82 ppm (t, J=7.0 Hz, 2H); 2.30 ppm (s, 6H).

EXAMPLE 6

N'-[2-[2-(dimethylamino)ethyl]-2H-pyrido[3',2':5,6]thiopyrano[4,3,2-cd]indazol-5-yl]—N,N-dimethyl-1,2-ethanediamine (X=N)

A mixture of the amino analogue of preparation 4 (0.50 g), 2-(dimethylamino)ethyl bromide hydrobromide (0.98 g) and potassium carbonate (1.37 g) in toluene (15 ml) was refluxed for 15 hrs. The mixture was cooled and the residue which was collected by filtration was triturated with hot acetonitrile. The insoluble material was removed by filtration through a celite bed. The filtrate was concentrated to 15 ml and allowed to stand overnight. The product was collected by filtration as a golden brown material (0.36 g). This crude material was dissolved in hot acetonitrile (10 ml), cooled to room temperature and placed in the refrigerator overnight. The product as golden brown needles was collected by filtration (0.26 g), m.p. 110–111° C.

$^1$H NMR in CDCl$_3$ 8.27 ppm (dd, J=1.6 Hz, J=4.7 Hz, 1H); 8.16 ppm (dd, J=1.6 Hz, J=7.7 Hz, 1H); 7.09 ppm (dd, J=4.7 Hz, J=7.7 Hz, 1H); 6.92 ppm (d, J=8.7 Hz, 1H); 6.87 ppm (d, J=7.1 Hz, 1H); 4.37 ppm (t, J=7.0 Hz, 2H); 325 ppm (t, J=5.9 Hz, 2H); 2.83 ppm (t, J=7.0 Hz, 2H); 2.60 ppm (t, J=5.9 Hz, 2H); 2.32 ppm (s, 6H); 2.34 ppm (s, 6H).

EXAMPLE 7

N'-[2-[2-(dimethylamino)lethyl]-2H-pyrido[3',2':5,6]thiopyrano[4,3,2-cd]indazol-5-yl]l-1,2-ethanediamine (X=N)

A commercial Red-Al solution (3.4 M in toluene, 0.6 ml) was added dropwise over a period of 3 minutes to a stirred suspension of the compound of the preparation 12 (100 mg) in toluene (1 ml) held at 70 ° C. The resultant bright red solution was heated for an additional 5 hrs at 70–75° C., cooled to room temperature and treated cautiously with a saturated aqueous ammonium chloride solution. The yellow suspension was diluted with dichloromethane (3 ml) and the mixture was filtered through a celite bed. The organic layer was dried over magnesium sulfate and concentrated to yield the crude product (100 mg). This material was purified by column chromatography over silica gel eluting sequentially with 2, 4, 8, 10 and 20% methanol in dichloromethane. The center eluents were concentrated to yield the product as a yellow solid (50 mg, m.p. 77–80° C.).

$^1$H—NMR in CDCl$_3$ 8.29 ppm (dd, J=1.7, 4.7 Hz, 1H); 8.17 ppm (dd, J=1.7, 7.8 Hz, 1H); 7.11 ppm (m, J=4.7, 7.8 Hz, 1H); 6.91 ppm (m, J=8.8, 8.8 Hz, 2H); 4.86 ppm (broad s, 1H); 4.36 ppm (t, J=7.0 Hz, 2H); 3.36 ppm (broad s, 4H); 2.82 ppm (t, J=6.9 Hz, 2H); 2.32 ppm (s, 6H); 1.48 ppm (s, 9H).

Dry hydrogen chloride was briefly passed through a solution of the title compound (50 mg) in chloroform (0.5 ml). Upon removal of the chloroform, the hydrochloride salt of the product was obtained as an orange solid (43 mg).

$^1$H-NMR in D$_2$O 8.23 ppm (dd, J=1.4, 4.8 Hz, 1H); 8.09 ppm (dd, J=1.4, 7.8 Hz, 1H); 7.26 ppm (m, J=4.9, 7.8 Hz, 1H); 7.13 ppm (d, J=8.8 Hz, 1H); 7.08 ppm (d, J=8.8 Hz, 1H); 4.71 ppm (t, J=5.9 Hz, 2H); 3.79 ppm (t, J=5.9 Hz, 2H); 3.59 ppm (t, J=6.2 Hz, 2H); 3.34 ppm (t, J=6.2 Hz, 2H); 3.05 ppm (s, 6H)

EXAMPLE 8

N'-[2-[2-(dimethylamino)ethyl-2H-pyrido[3',4':5,6] thiopyrano[4.3,2-cd]indazol-5-yl]-1,2-ethanediamine (Z=N)

According to the procedure of example 7, starting from the intermediate of preparation 8, the title compound as hydrochloride salt is prepared.

$^1$H-NMR in D$_2$O 9.01 ppm (s, 1H); 8.39 ppm (d, J=6.5 Hz, 1H); 7.90 ppm (d, J=6.5 Hz, 1H); 7.39 ppm (d, J=8.9 Hz, 1H); 7.27 ppm (d, J=8.9 Hz, 1H); 486 ppm (t, J=5.9 Hz, 2H); 3.88 ppm (t, J=5.8 Hz, 2H); 3.62 ppm (t, J=6.2 Hz, 2H); 3.36 ppm (t, J=6.2 Hz, 2H); 3.09 ppm (s, 6H).

EXAMPLE 9

Compounds (I)

Following the methods described in example 6 or in example 7, starting from the appropriate amine analogues obtained according to example 5 and from the appropriate aminoalkyl halide (method of example 6) or alternatively from aminoacids or derivative thereof (method of example 7), the following compounds of formula (I) are prepared:

(1) N'-[2-[2-(diethylamino)ethyl]-2H-pyrido[3',2:5,6] thiopyrano[4,3,2-cd]indazol 5-yl]-N,N-dimethyl-1,2-ethanediamine;

(2) N'-[2-[2-(methylamino)ethyl]-2H-pyrido[3',2':5,6] thiopyrano[4,3,2-cd]indazol 5-yl]-N,N-dimethyl-1,2-ethanediamine;

(3) N'-[2-[2-aminoethyl]-2H-pyrido[3',2':5,6]thiopyrano[4,3,2-cd]indazol-5-yl ]-N,N-dimethyl-1,2-ethanediamine;

(4) N'-[2-[2-(2-hydroxyethylamino)ethyl]-2H-pyrido[3',2':5,6]thiopyrano[4,3,2-cd]indazol-5-yl]-N,N-dimethyl-1,2-ethanediamine;

(5) N'-[2-[2-(dimethylamino)ethyl]-2H-pyrido[3',2':5,6] thiopyrano[4,3,2-cd]indazol-5-yl]-1,2-ethanediamine, $^1$H N.M.R. (200 MHz) in D$_2$ O 8.69 ppm (s, 1H); 8.49 ppm (d, J=5.7 Hz, 1H); 8.22 ppm (d, J=5.7 Hz, 1H); 7.39 ppm (d, J=8.7 Hz, 1H); 7.27 ppm (d, J=8.5 Hz, 1H); 4.90 ppm (t, J=5.8 Hz, 2H); 3.91 ppm (t, J=5.8 Hz, 2H); 3.63 ppm (t, J=5.8 Hz, 2H); 3.35 ppm (t, J=5.8 Hz, 2H); 3.0 ppm (s, 6H);

(6) N'-[2-[2-(diethylamino)ethyl]-2H-pyrido[3',2':5,6] thiopyrano[4,3,2-cd]indazol-5-yl]-1,2-ethanediamine;

(7) N'-[2-[2-(methylamino)ethyl]-2H-pyrido[3',2':5,6] thiopyrano[4,3,2cd]indazol-5-yl]-1,2ethanediamine;

(8) N'-[2-[2-aminoethyl]-2H-pyrido(3',2':5,6]thiopyrano(4,3,2-cd]indazol-5-yl]-1,2- ethanediamine;

(9) N'-[2-[2-(2-hydroxyethylamino)ethyl]-2H-pyrido[3',2':5,6]thiopyrano[4,3,2-cd]indazol-5-yl]-1,2-ethanediamine;

(10) N'-[2-[2-(dimethylamino)ethyl]-2H-pyrido[3',2':5,6] thiopyrano[4,3,2-cd]indazol-5-yl]-N-methyl-1,2-ethanediamine, m.p. 114–115° C., $^1$H N.M.R. in CDCl$_3$8.27 ppm (dd, J=4.7 Hz, J=7.8 Hz, 1H); 8.14 ppm (dd, J=1.8 Hz, J=7.8 Hz, 1H); 7.08 ppm (dd, J=4.7 Hz, J=7.8 Hz, 1H); 6.89 ppm (d, J=8.7 Hz, 1H); 6.88 ppm (d, J=8.7 Hz, 1H); 4.34 ppm (t, J=7.1 Hz, 2H); 3.30 ppm (t, J=5.7 Hz, 2H); 2.86 ppm (t, J=5.7 Hz, 2H); 2.80 ppm (t, J=7.1 Hz, 2H); 2.47 ppm (s, 3H);2.30 ppm (s, 6H);

(11) N'-[2-[2-(diethylamino)ethyl]-2H-pyrido[3',2':5,6] thiopyrano[4,3,2-cd]indazol-5-yl]—N-methyl-1,2-ethanediamine, m.p. 120–124° C., $^1$H N.M.R. in CDCl$_3$ 9.07 ppm (s, 1H); 8.23 ppm (d, J=5.4 Hz, 1H); 7.11 ppm (d, J=5.4 Hz, 1H); 6.93 ppm (d, J=8.8 Hz, 1H); 6.86 ppm (d, J=8.8 Hz, 1H); 5.42 ppm (br s, 1H); 4.36 ppm (t, J=7.1 Hz, 2H); 3.36 ppm (t, J=5.6 Hz, 2H); 2.96 ppm (t, J=7.1 Hz, 2H); 2.93 ppm (t, J=5.5 Hz, 2H); 2.62 ppm (q, J=7.1 Hz, 4H); 2.59 ppm (s, 3H); 1.02 ppm (t, J=7.1, Hz 6H);

(12) N'-[2-[2-(methylamino)ethyl]-2H-pyrido[3',2':5,6] thiopyrano[4,3,2-cd]indazol-5-yl]-N-methyl-1,2-ethanediamine;

(13) N'-[2-[2-aminoethyl]-2H-pyrido[3',2':5,6]thiopyrano[4,3,2-cd]indazol-5-yl]-N-methyl-1,2-ethanediamine;

(14) N'-[2-[2-(2-hydroxyethylamino)ethyl]-2H-pyrido[3',2':5,6]thiopyrano[4,3,2-cd]indazol-5-yl]-N-methyl-1,2-ethanediamine;

(15) N'-[2-[2-(dimethylamino)ethyl]-2H-pyrido[3',2':5,6] thiopyrano[4,3,2-cd]indazol-5-yl]-N-hydroxyethyl-1,2-ethanediamine;

(16) N'-[2-[2-(diethylamino)ethyl]-2H-pyrido[3',2':5,6] thiopyrano[4,3,2,-cd]indazol-5-yl]-N-hydroxyethyl-1,2-ethanediamine;

(17) N'-[2-[2-(methylamino)ethyl]-2H-pyrido[3',2':5,6] thiopyrano[4,3,2-cd]indazol-5-yl]-N-hydroxyethyl-1,2-ethanediamine;

(18) N'-[2-[2-aminoethyl]-2H-pyrido[3',2':5,6]thiopyrano[4,3,2-cd]indazol-5-N-hydroxyethyl -1,2-ethanediamine;

(19) N'-[2-[2-(2-hydroxyethylamino)ethyl]-2H-pyrido[3',2':5,6]thiopyrano[4,3,2-cd]indazol-5-yl]-N-hydroxyethyl-1,2-ethanediamine;

(20) N-[2-[2-(dimethylamino)ethyl]-2H-pyrido[3',2':5,6] thiopyrano[4,3,2-cd]indazol-5-yl]-2-aminoethanol;

(21) N-[2-[2-(diethyiamino)ethyl]-2H-pyrido[3',2':5,6] thiopyrano[4,3,2-cd]indazol-5-yl]-2-aminoethanol;

(22) N-[2-[2-(methylamino)ethyl]-2H-pyrido[3',2':5,6] thiopyrano[4,3,2-cd]indazol-5-yl]-2-aminoethanol;

(23) N-[2-[2-aminoethyl]-2H-pyrido[3',2':5,6]thiopyrano[4,3,2-cd]indazol-5-yl]-2-aminoethanol;

(24) N-[2-[2-(2-hydroxyethylamino)ethyl]-2H-pyrido[3',2':5,6]thiopyrano[4,3,2-cd]indazol-5-yl]-2-aminoethanol;

(25) N'-[2-[2-(dimethylamino)ethyl]-2H-pyrido[4',3':5,6] thiopyrano[4,3,2-cd]indazol-5-yl]-N,N-dimethyl-1,2-ethanediamine;

(26) N'-[2-[2-(diethylamino)ethyl]-2H-pyrido[4',3':5,6] thiopyrano[4,3,2-cd]indazol-5-yl]-N,N-dimethyl-1,2-ethanediamine;

(27) N'-[2-[2-(methylamino)ethyl]-2H-pyrido[4',3':5,6] thiopyrano[4,3,2-cd]indazol-5-yl]-N,N-dimethyl-1,2-ethanediamine;

(28) N'-[2-[2-aminoethyl]-2H-pyrido[4',3':5,6]thiopyrano[4,3,2-cd]indazol-N,N-dimethyl-1,2-ethanediamine;

(29) N'-[2-[2-(2-hydroxyethylamino)ethyl]-2H-pyrido[4',3':5,6]thiopyrano[4,3,2-cd]indazol-5-yl]-N,N-dimethyl-1,2-ethanediamine;

(30) N'-[2-[2-(dimethylamino)ethyl]-2H-pyrido[4',3':5,6]thiopyrano[4,3,2-cd]indazol-5-yl]-1,2-ethanediamine;

(31) N'-[2-[2-(diethylamino)ethyl]-2H-pyrido[4',3':5,6]thiopyrano[4,3,2-cd]indazol-5-yl]-1,2-ethanediamine;

(32) N'-[2-[2-(methylamino)ethyl]-2H-pyrido[4',3':5,6]thiopyrano[4,3,2-cd]indazol-5-yl]-1,2-ethanediamine;

(33) N'-[2-[2-aminoethyl]-2H-pyrido[4',3':5,6]thiopyrano[4,3,2-cd]indazol-5-yl-1,2-ethanediamine;

(34) N'-[2-[2-(2-hydroxyethylamino)ethyl]-2H-pyrido[4',3':5,6]thiopyrano[4,3,2-cd]indazol-5-yl]-1,2ethanediamine;

(35) N'-[2-[2-(dimethylamino)ethyl]-2H-pyrido[4',3':5,6]thiopyrano[4,3,2-cd]indazol-5-yl]-N-methyl-1,2-ethanediamine;

(36) N'-[2-[2-(diethylamino)ethyl]-2H-pyrido[4',3':5,6]thiopyrano[4,3,2cd]indazol-5-yl]-N-methyl-1,2ethanediamine;

(37) N'-[2-[2-(methylamino)ethyl]-2H-pyrido[4',3':5,6]thiopyrano[4,3,2cd]indazol-5-yl]-N-methyl-1,2-ethanediamine;

(38) N'-[2-[2-aminoethyl]-2H-pyrido[4',3':5,6]thiopyrano[4,3,2-cd]indazol-5-yl]-N-methyl-1,2-ethanediamine;

(39) N'-[2-[2-(2-hydroxyethylamino)ethyl]-2H-pyrido[4',3':5,6]thiopyrano[4,3,2-cd]indazol-5-yl]-N-methyl-1,2-ethanediamine;

(40) N'-[2-[2-(dimethylamino)ethyl]-2H-pyrido[4',3':5,6]thiopyrano[[4,3,2-cd]indazol-5-yl]-N-hydroxyethyl-1,2-ethanediamine;

(41) N'-[2-[2-(diethylamino)ethyl]-2H-pyrido[4',3':5,6]thiopyrano[4,3,2cd]indazol-5-yl]-N-hydroxyethyl-1,2-ethanediamine;

(42) N'-[2-[2-(methylamino)ethyl]-2H-pyrido[4',3':5,6]thiopyrano[4,3,2-cd]indazol-5-yl]-N-hydroxyethyl-1,2-ethanediamine;

(43) N'-[2-[2-aminoethyl]-2H-pyrido(4',3':5,6]thiopyrano[4,3,2-cd]indazol-5-yl]-N-hydroxyethyl-1,2-ethanediamine;

(44) N'-[2-[2-(2-hydroxyethylamino)ethyl]-2H-pyrido[4',3':5,6]thiopyrano 4,3,2-cd]indazol-5-yl]-N-hydroxyethyl-1,2-ethanediamine;

(45) N-[2-[2-(dimethylamino)ethyl]-2H-pyrido[4', 3':5,6]thiopyrano[4,3,2-cd]indazol-5-yl]-2-aminoethanol;

(46) N-[2-[2-(diethyiamino)ethyl]-2H-pyrido[4',3':5,6]thiopyrano[4,3,2-cd]indazol-5-yl]-2-aminoethanol;

(47) N-[2-[2-(methylamino)ethyl]-2H-pyrido[4',3':5,6]thiopyrano[4,3,2-cd]indazol-5-yl]-2-aminoethanol;

(48) N-[2-[2-aminoethyl]-2H-pyrido[4',3':5,6]thiopyrano[4,3,2-cd]indazol-5-yl]-2-aminoethanol;

(49) N-[2-[2-(2-hydroxyethylamino)ethyl]-2H-pyrido[4',3':5,6]thiopyrano[4,3,2-cd]indazol-5-yl]-2-aminoethanol;

(50) N'-[2-[2-(dimethylamino)ethyl]-2H-pyrido[3',4':5,6]thiopyrano[4,3,2-cd]indazol-5-yl]-N,N-dimethyl-1,2-ethanediamine, $^1$H N.M.R. (200 MHz) in CDCl$_3$ 9.09 ppm (s, 1H); 8.25 ppm (d, J=5.3 Hz, 1H); 7.15 ppm (d, J=5.4 Hz, 1H); 6.99 ppm (d, J=8.8 Hz, 1H); 6.90 ppm (d, J=8.8 Hz, 1H); 4.45 ppm (t, J=6.9 Hz, 2H); 3.34 ppm (t, J=5.9 Hz, 2H); 3.00 ppm (t, J=6.9 Hz, 2H); 2.87 ppm (t, J=5.9 Hz, 2H); 2.45 ppm (s, 6H); 3.29 ppm (s, 6H);

(51) N'-[2-[2-(diethylamino)ethyl]-2H-pyrido[3',4':5,6]thiopyrano[4,3,2-cd]indazol-5-yl -N,N-dimethyl-1,2-ethanediamine, $^1$H N.M.R. (200 MHz) in CDCl$_3$ 8.29 ppm (dd, J=1.8 Hz, J=3.8 Hz, 1H); 8.16 ppm (dd, J=1.8 Hz, J=7.8 Hz, 1H); 7.10 ppm (dd, J=4.7 Hz, J=7.3 Hz, 1H); 6.97 ppm (d, J=8.8 Hz, 1H); 6.89 ppm (d, J=8.8 Hz, 1H); 4.41 ppm (t, J=7.1 Hz, 2H); 3.33 ppm (t, J=6.1 Hz, 2H); 3.04 ppm (t, J=7.1 Hz, 2H); 2.71 ppm (m, 6H); 2.33 ppm (s, 6H); 1.05 ppm (t, 6H);

(52) N'-[2-[2-(methylamino)ethyl]-2H-pyrido[3',4':5,6]thiopyrano[4,3,2-cd]indazol-5-yl]-N,N-dimethyl-1,2-ethanediamine;

(53) N'-[2-[2-aminoethyl]-2H-pyrido[3',4':5,6]thiopyrano[4,3,2-cd]indazol-5-yl]-N,N-dimethyl-1,2-ethanediamine;

(54) N'-[2-[2-(2-hydroxyethylamino)ethyl]-2H-pyrido[3',4':5,6]thiopyrano[4,3,2-cd]indazol-5-yl]-N,N-dimethyl-1,2-ethanediamine;

(55) N'-[2-[2-(diethylamino)ethyl]-2H-pyrido[3',4':5,6]thiopyrano[4,3,2-cd]indazol-5-yl]-1,2-ethanediamine;

(56) N'-[2-[2-(methylamino)ethyl]-2H-pyrido[3',4':5,6]thiopyrano[4,3,2-cd ]indazol-5-yl]-1,2-ethanediamine;

(57) N'-[2-[2-aminoethyl]-2H-pyrido[3',4':5,6]thiopyrano[4,3,2-cd]indazol-5-yl -]-1,2-ethanediamine;

(58) N'-[2-[2-(2-hydroxyethylamino)ethyl]-2H-pyrido(3',4':5,6]thiopyrano[4,3,2-cd]indazol-5-yl]-1,2-ethanediamine;

(59) N'-[2-[2-(dimethylamino)ethyl]-2H-pyrido[3'4':5,6]thiopyrano[4,3,2-cd]indazol-5-yl]-N-methyl-1,2-ethanediamine;

(60) N'-[2-[2-(diethylamino)ethyl]2H-pyrido[3',4':5,6]thiopyrano[4,3,2-cd]indazol-5-yl]-N-methyl-1,2-ethanediamine;

(61) N'-[2-[2-(methylamino)ethyl]-2H-pyrido[3',4':5,6]thiopyrano[4,3,2cd]indazol-5-yl]-N-methyl-1,2-ethanediamine;

(62) N'-[-2-[2-aminoethyl]-2H-pyrido[3',4':5,6]thiopyrano[4,3,2-cd]indazol-5-yl]-N-methyl-1,2ethanediamine;

(63) N'-[2-[2-(2-hydroxyethylamino)ethyl]-2H-pyrido[3',4':5,6]thiopyrano [4,3,2-cd]indazol-5-yl]-N-methyl-1,2-ethanediamine;

(64) N'-[2-[2-(dimethylamino)ethyl]-2H-pyrido[3',4':5,6]thiopyrano[4,3,2-cd]indazol-5-yl]-N-hydroxyethyl-1,2-ethanediamine;

(65) N'-[2-[2-(diethylamino)ethyl]-2H-pyrido[3',4':5,6]thiopyrano[4,3,2cd]indazol-5-yl]-N-hydroxyethyl -1,2-ethanediamine;

(66) N'-[2-[2-(methylamino)ethyl]-2H-pyrido[3',4':5,6]thiopyrano[4,3,2-cd]indazol-5-yl]-N-hydroxyethyl-1,2-ethanediamine;

(67) N'-[2-[2-aminoethyl]-2H-pyrido[3',4':5,6]thiopyrano[4,3,2-cd]indazol-5-yl]-N-hydroxyethyl-1,2-ethanediamine;

(68) N'-[2-[2-(2-hydroxyethylamino)ethyl]-2H-pyrido[3',4':5,6]thiopyrano[4,3,2-cd]indazol-5-yl]-N-hydroxyethyl-1,2-ethanediamine;

(69) N-[2-[2-(dimethylamino)ethyl]-2H-pyrido[3',4':5,6]thiopyrano[4,3,2-cd]indazol-5-yl]-2-aminoethanol;

(70) N-[2-[2-(diethylamino)ethyl]-2H-pyrido[3',4'5,6]thiopyrano[4,3,2-cd]indazol-5-yl]-2-aminoethanol;

(71) N-[2-[2-(methylamino)ethyl]-2H-pyrido[3',4':5,6]thiopyrano[4,3,2-cd]indazol-5-yl]-2-aminoethanol;

(72) N-[2-[2-aminoethyl]-2H-pyrido[3',4':5,6]thiopyrano[4,3,2-cd]indazol-5-yl]-2-aminoethanol;

(73) N-[2-[2-(2-hydroxyethylamino)ethyl]-2H-pyrido[3',4':5,6]thiopyrano[4,3,2-cd]indazol-5-yl]-2-aminoethanol;

(74) N'-[2-[2-(dimethylamino)ethyl]-2H-pyrido[2',3':5,6]thiopyrano[4,3,2-cd]indazol-5-yl]-N,N-dimethyl-1,2-ethanediamine;

(75) N'-[2-[2-(diethylamino)ethyl]-2H-pyrido[2',3':5,6]thiopyrano[4,3,2cd]indazol-5-yl]-N,N-dimethyl-1,2-ethanediamine;

(76) N'-[2-[2-(methylamino)ethyl]-2H-pyrido[2',3':5,6]thiopyrano[4,3,2-cd]indazol-5-yl]-N,N-dimethyl-1,2-ethanediamine;

(77) N'-[2-[2-aminoethyl]-2H-pyrido[2',3':5,6]thiopyrano[4,3,2d]indazol-5-yl]-N,N-dimethyl-1,2-ethanediamine;
(78) N'-[2-[2-(2-hydroxyethylamino)ethyl]-2H-pyrido[2',3':5,6]thiopyrano[4,3,2-cd]indazol-5-yl]-N,N-dimethyl-1,2-ethanediamine;
(79) N'-[2-[2-(dimethylamino)ethyl]-2H-pyrido[2',3':5,6]thiopyrano[4,3,2-cd]indazol-5-yl]-1,2-ethanediamine;
(80) N'-[2-[2-(diethylamino)ethyl]-2H-pyrido[2',3':5,6]thiopyrano[4,3,2-cd]indazol-5-yl]-1,2-ethanediamine;
(81) N'-[2-[2-(methylamino)ethyl]-2H-pyrido[2',3':5,6]thiopyrano[4,3,2-cd]indazol-5-yl]-1,2-ethanediamine;
(82) N'-[2-[2-aminoethyl]-2H-pyrido[2',3':5,6]thiopyrano[4,3,2-cd]indazol-5-yl]-1,2-ethanediamine;
(83) N'-[2-[2-(2-hydroxyethylamino)ethyl]-2H-pyrido[2',3':5,6]thiopyrano[4,3,2-cd]indazol-5-yl]-1,2-ethanediamine;
(84) N'-[2-[2-(dimethylamino)ethyl]-2H-pyrido[2',3':5,6]thiopyrano[4,3,2-cd]indazol-5-yl]-N-methyl-1,2-ethanediamine;
(85) N'-[2-[2-(diethylamino)ethyl]-2H-pyrido[2',3':5,6]thiopyrano[4,3,2-cd]indazol-5-yl]-N-methyl-1,2-ethanediamine;
(86) N'-[2-[2-(methylamino)ethyl]-2H-pyrido[2',3':5,6]thiopyrano[4,3,2-cd]indazol-5-yl]-N-methyl-1,2-ethanediamine;
(87) N'-[2-[2-aminoethyl]-2H-pyrido[2',3':5,6]thiopyrano[4,3,2-cd]indazol-5-yl]-N-methyl-1,2-ethanediamine;
(88) N'-[2-[2-(2-hydroxyethylamino)ethyl]-2H-pyrido[2',3':5,6]thiopyrano[4,3,2-cd]indazol-5-yl]-N-methyl-1,2-ethanediamine;
(89) N'-[2-[2-(dimethylamino)ethyl]-2H-pyrido[2',3':5,6]thiopyrano[4,3,2-cd]indazol-5-yl]-N-hydroxyethyl-1,2-ethanediamine;
(90) N'-[2-[2-(diethylamino)ethyl]-2H-pyrido[2',3':5,6]thiopyrano[4,3,2-cd]indazol-5-yl]-N-hydroxyethyl-1,2-ethanediamine;
(91) N'-[2-[2-(methylamino)ethyl]-2H-pyrido[2',3':5,6]thiopyrano[4,3,2cd]indazol-5-yl]-N-hydroxyethyl-1,2-ethanediamine;
(92) N'-[2-[2-aminoethyl]-2H-pyrido[2',3':5,6]thiopyrano[4,3,2-cd]indazol-5-yl]-N-hydroxyethyl-1,2-ethanediamine;
(93) N'-[2-[2-(2-hydroxyethylamino)ethyl]-2H-pyrido[2',3':5,6]thiopyrano[4,3,2-cd]indazol-5-yl]-N-hydroxyethyl-1,2-ethanediamine;
(94) N-[2-[2-(dimethylamino)ethyl]-2H-pyrido[2',3':5,6]thiopyrano[4,3,2-cd]indazol-5-yl]-2-aminoethanol;
(95) N-[2-[2-(diethylamino)ethyl]-2H-pyrido[2',3':5,6]thiopyrano[4,3,2-cd]indazol-5-yl]-2-aminoethanol;
(96) N-[2-[2-(methylamino)ethyl]-2H-pyrido[2',3':5,6]thiopyrano[4,3,2d]indazol-5-yl]-2-aminoethanol;
(97) N-[2-[2-aminoethyl]-2H-pyrido[2',3':5,6]thiopyrano[4,3,2-cd]indazol-5-yl]-2-aminoethanol;
(98) N-[2-[2-(2-hydroxyethylamino)ethyl]-2H-pyrido[2',3':5,6]thiopyrano[4,3,2-cd]indazol-5-yl]-2-aminoethanol.

EXAMPLE 10

Compounds (I), D=—NHCO—CH$_2$—NR$_2$R$_3$

Starting from a chloroform solution of the suitable compounds prepared according to preparations 7 or 8, by removal of the N-BOC protecting group with dry gaseous hydrogen chloride, the following compounds as hydrochloride salts are obtained:

(1) N'-[2-(2-dimethylamino)ethyl]-5-(2'-amino-acetylamino)- 2H-pyrido[3',2':5,6]thiopyrano [4,3,2-cd]indazole, $^1$H N.M.R. (200 MHz) in D$_2$O 3.0 ppm (s, 6H); 3.81 ppm (t, 2H); 4.13 ppm (t, 2H); 4.80 ppm (s, 2H); 7.30 ppm (m, 3H); 8.30 ppm (m, 2H);
(2) N'-[2-(2-dimethylamino)ethyl]-5-(2'-amino-acetylamino)-2H-pyrido[3',4':5,6]thiopyrano [4,3,2-cd]indazole;
(3) N'-[2-(2-dimethylamino)ethyl]-5-(2'-amino-acetylamino)-2H-pyrido[4',3':5,6]thiopyrano [4,3,2-cd]indazole;
(4) N'-[2-(2dimethylamino)ethyl]-5-(2'-amino-acetylamino)-2H-pyrido[2',3':5,6]thiopyrano [4,3,2-cd]indazole;
(5) N'-[2-(2-diethylamino)ethyl]-5-(2'-amino-acetylamino)-2H-pyrido(3',2':5,6]thiopyrano [4,3,2-cd]indazole;
(6) N'-[2-(2-diethylamino)ethyl]-5-(2'-amino-acetylamino)-2H-pyrido[3',4':5,6]thiopyrano [4,3,2-cd]indazole;
(7) N'-[2-(2-diethylamino)ethyl]-5-(2'-amino-acetylamino)-2H-pyrido[4',3':5,6]thiopyrano [4,3,2-cd]indazole;
(8) N'-[2-(2-diethylamino)ethyl]-5-(2'-amino-acetylamino)-2H-pyrido[2',3':5,6]thiopyrano [4,3,2-cd]indazole;
(9) N'-[2-(2-methylamino)ethyl]-5-(2'-amino-acetylamino)-2H-pyrido[3',2':5,6]thiopyrano [4,3,2-cd]indazole;
(10) N'-[2-(2-methylamino)ethyl]-5-(2'-amino-acetylamino)-2H-pyrido[3',4':5,6]thiopyrano [4,3,2-cd]indazole;
(11) N'-[2-(2-methylamino)ethyl]-5-(2'-amino-acetylamino)-2H-pyrido[4',3':5,6]thiopyrano [4,3,2-cd]indazole;
(12) N'-[2-(2-methylamino)ethyl]-5-(2'amino-acetylamino)-2H-pyrido[2',3':5,6]thiopyrano [4,3,2-cd]indazole;
(13) N'-[2-aminoethyl]-5-(2'amino-acetylamino)-2H-pyrido [3',2':5,6]thiopyrano[4,3,2-cd]indazole;
(14) N'-[2-aminoethyl]-5-(2'amino-acetylamino)-2H-pyrido [3',4':5,6]thiopyrano[4,3,2-cd]indazole;
(15) N'-[2-aminoethyl]-5-(2'amino-acetylamino)-2H-pyrido [4',3':5,6]thiopyrano[4,3,2-cd]indazole;
(16) N'-[2-aminoethyl]-5-(2'amino-acetylamino)-2H-pyrido [2',3':5,6]thiopyrano[4,3,2-cd]indazole;
(17) N'-[2-(2-hydroxyethylamino)ethyl]-5-(2'amino-acetylamino)-2H-pyrido[3',2':5,6] thiopyrano [4,3,2-cd]indazole;
(18) N'-[2-(2- hydroxyethylamino)ethyl]-5-(2'amino-acetylamino)-2H-pyrido[3',4':5,6 thiopyrano [4,3,2-cd]indazole;
(19) N'-[2-(2- hydroxyethylamino)ethyl]-5-(2'amino-acetylamino)-2H-pyrido[4',3':5,6] thiopyrano [4,3,2-cd]indazole;
(20) N'-[2-(2- hydroxyethylamino)ethyl]-5-(2'amino-acetylamino)-2H-pyrido[2',3':5,6] thiopyrano [4,3,2-cd]indazole.

EXAMPLE 11

Compounds (I). D=nitro

According to the procedures described in examples 1, 3 or 4, starting from the suitable intermediates, the following nitro derivatives are obtained:

(1) N,N-diethyl-5-nitro-2 H-pyrido[3',4': 5,6]thiopyrano[4,3,2-cd]indazole-2-ethanamine, $^1$H N.M.R. (200 MHz) in CDCl$_3$ 9.38 ppm (s, 1H); 8.50 ppm (d, J=5.4 Hz, 1H); 8.23 ppm (d, J=9.3 Hz, 1H); 7.45 ppm (d, J=5.4 Hz, 1H); 7.11 ppm (d, J=9.3 Hz, 1 h); 4.45 ppm (t, J=6.4 Hz, 2H); 2.98 ppm (t, J=6.4 Hz, 2H); 2.54 ppm (q, J=7.1 Hz, 4H); 0.92 ppm (t, J=7.1 Hz, 6H);
(2) N,N-diethyl-5-nitro-2H-pyrido[3',2':5,6]thiopyrano[4,3,2-cd]indazole-2-ethanamine, m.p. 132–133° C., $^1$H N.M.R. (200 MHz) in CDCl$_3$ 8.56 ppm (dd, J=1.7 Hz, J=4.6 Hz, 1H); 8.43 ppm (dd, J=1.7 Hz, J=7.8 Hz, 1H); 8.25 ppm (d, J=9.3 Hz, 1H); 7.33 ppm (dd, J=4.6 Hz, J=7.8 Hz, 1H); 7.08 ppm (d, J=9.3 Hz, 1H); 4.44 ppm (t, J=6.4 Hz, 2H); 2.98 ppm (t, J=6.4 Hz, "h9; 2.54 ppm (q, J=7.1 Hz, 4H); 0.94 ppm (t, J=7.1 Hz, 6H);
(3) N,N-dimethyl-5-nitro-2H-pyrido[4',3':5,6]thiopyrano[4,3,2-cd]indazole-2-ethanamine;
(4) N,N-diethyl-5-nitro-2H-pyrido[4',3':5,6]thiopyrano[4,3,2-cd]indazole-2-ethanamine;

23

(5) N,N-dimethyl-5-nitro-2H-pyrido[2',3':5,6]thiopyrano[4,3,2-cd]indazole-2-ethanamine;
(6) N,N-diethyl-5-nitro-2H-pyrido[2',3':5,6]thiopyrano[4,3,2-cd]indazole-2-ethanamine;
(7) N-methyl-5-nitro-2H-pyrido[3',4':5,6]thiopyrano[4,3,2-cd]indazole-2-ethanamine;
(8) N-methyl-5-nitro-2H-pyrido[3',2':5,6]thiopyrano[4,3,2-cd]indazole-2-ethanamine;
(9) N-methyl-5-nitro-2H-pyrido[4',3':5,6]thiopyrano[4,3,2-cd]indazole-2-ethanamine;
(10) N-methyl-5-nitro-2H-pyrido[2',3':5,6]thiopyrano[4,3,2-cd]indazole-2-ethanamine;
(11) 5-nitro-2H-pyrido[3',4':5,6]thiopyrano[4,3,2-cd]indazole-2-ethanamine;
(12) 5-nitro-2H-pyrido[3',2':5,6]thiopyrano[4,3,2-cd]indazole-2-ethanamine;
(13) 5-nitro-2H-pyrido[4',3':5,6]thiopyrano[4,3,2-cd]indazole-2-ethanamine;
(14) 5-nitro-2H-pyrido[2',3':5,6]thiopyrano[4,3,2-cd]indazole-2-ethanamine;
(15) N-hydroxyethyl-5-nitro-2H-pyrido[3',4':5,6]thiopyrano[4,3,2-cd]indazole-2-ethanamine;
(16) N-hydroxyethyl-5-nitro-2 H-pyrido[3',2':5,6]thiopyrano[4,3,2-cd]indazole-2-ethanamine;
(17) N-hydroxyethyl-5-nitro-2H-pyrido[4',3':5,6]thiopyrano[4,3,2-cd]indazole-2-ethanamine;
(18) N-hydroxyethyl-5-nitro-2H-pyrido[2',3':5,6]thiopyrano[4,3,2-cd]indazole-2-ethanamine.

EXAMPLE 12

Compounds (I), D=amino

According to the procedure described in examples 2 or 5, starting from the nitro derivatives of example 11, the following amino derivatives are obtained:
(1) N,N-diethyl-5-amino-2H-pyrido[3',4':5,6]thiopyrano[4,3,2-cd]indazole-2-ethanamine, $^1$H N.M.R. (200 MHz) in CDCl$_3$ 9.09 ppm (s, 1H); 8.24 ppm (d, J=5.5 Hz, 1H); 7.13 ppm (d, J=5.5 Hz, 1H); 6.88 ppm (d, J=8.6 Hz, 1H); 6.77 ppm (d, J=8.6 Hz, 1H); 4.31 ppm (t, J=7.9 Hz, 2H); 3.33 ppm (br s, 2H); 2.92 ppm (t, J=7.0 Hz, 2H); 2.58 ppm (q, J=7.1 Hz, 4H); 1.01 ppm (t, J=7.1 Hz, 6H);
(2) N,N-diethyl-5-amino-2H-pyrido[3',2': 5,6]thiopyrano[4,3,2-cd]indazole-2-ethanamine;
(3) N,N-dimethyl-5-amino-2H-pyrido[4',3':5,6]thiopyrano[4,3,2-cd]indazole-2-ethanamine;
(4) N,N-diethyl-5-amino-2H-pyrido[4',3':5,6]thiopyrano[4,3,2-cd]indazole-2-ethanamine;
(5) N,N-dimethyl-5-amino-2H-pyrido[2',3':5,6]thiopyrano[4,3,2-cd]indazole-2-ethanamine;
(6) N,N-diethyl-5-amino-2H-pyrido[2',3':5,6]thiopyrano[4,3,2-cd]indazole-2-ethanamine;
(7) N-methyl-5-amino-2H-pyrido[3',4':5,6]thiopyrano[4,3,2-cd]indazole-2-ethanamine;
(8) N-methyl-5-amino-2H-pyrido[3',2':5,6]thiopyrano[4,3,2-cd]indazole-2-ethanamine;
(9) N-methyl-5-amino-2H-pyrido[4',3':5,6]thiopyrano[4,3,2-cd]indazole-2-ethanamine;
(10) N-methyl-5-amino-2H-pyrido[2',3':5,6]thiopyrano[4,3,2-cd]indazole-2-ethanamine;
(11) 5-amino-2H-pyrido[3',4':5,6]thiopyrano[4,3,2-cd]indazole-2-ethanamine;
(12) 5-amino-2H-pyrido[3',2':5,6]thiopyrano[4,3,2-cd]indazole-2-ethanamine;
(13) 5-amino-2H-pyrido[4',3':5,6]thiopyrano[4,3,2-cd]indazole-2-ethanamine;
(14) 5-amino-2H-pyrido[2',3':5,6]thiopyrano[4,3,2-cd]indazole-2-ethanamine;
(15) N-hydroxyethyl-5-amino-2H-pyrido[3',4':5,6]thiopyrano[4,3,2-cd]indazole-2-ethanamine;
(16) N-hydroxyethyl-5-amino-2H-pyrido[3',2':5,6]thiopyrano[4,3,2-cd]indazole-2-ethanamine;
(17) N-hydroxyethyl-5-amino-2H-pyrido[4',3':5,6]thiopyrano[4,3,2-cd]indazole-2-ethanamine;
(18) N-hydroxyethyl-5-amino-2H-pyrido[2',3':5,6]thiopyrano[4,3,2-cd]indazole-2-ethanamine.

TABLE II

| Structure | Example | IC$_{50}$ ($\mu$g/ml) | | | |
| --- | --- | --- | --- | --- | --- |
| | | L1210 | S180 | LoVo | LoVo/Dx |
| 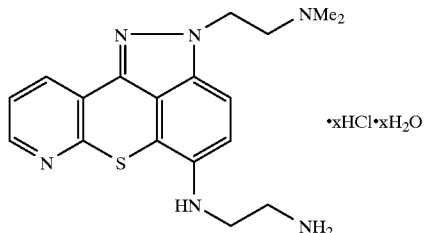 ·xHCl·xH$_2$O | 7 | 0.0125 | 0.058 | 0.027 | 16.8 |
| 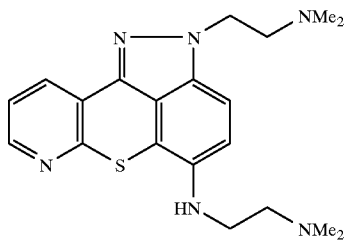 | 6 | 0.008 | 0.028 | 2.4 | 2.6 |

TABLE II-continued

| Structure | Example | IC$_{50}$ ($\mu$g/ml) | | | |
| --- | --- | --- | --- | --- | --- |
| | | L1210 | S180 | LoVo | LoVo/Dx |
| (structure with NMe$_2$, •xHCl•xH$_2$O, HN-CH$_2$-C(O)-NH$_2$) | ex. 10-cpd 1 | 0.03 | 0.22 | n.d. | n.d. |
| (structure with NMe$_2$, •xHCl•xH$_2$O, HN-CH$_2$CH$_2$-NH$_2$) | ex.9-cpd 30 | 0.014 | 0.058 | n.d. | n.d. |
| (structure with NMe$_2$, •xHCl•xH$_2$O, HN-C(O)-CH$_2$-NH$_2$) | ex. 10-cpd 2 | n.d. | n.d. | 0.04 | 0.21 |
| (structure with NMe$_2$, •xHCl•xH$_2$O, HN-CH$_2$CH$_2$-NH$_2$) | 8 | 0.0016 | 0.0029 | 0.008 | 0.26 |
| (structure with NMe$_2$, NH$_2$) | 5 | 0.0030 | 0.0066 | 0.016 | 0.027 |

TABLE II-continued

| Structure | Example | IC$_{50}$ ($\mu$g/ml) | | | |
| --- | --- | --- | --- | --- | --- |
| | | L1210 | S180 | LoVo | LoVo/Dx |
| [structure with NEt$_2$, NH$_2$] | ex. 12-cpd 1 | 0.0015 | 0.0031 | 0.036 | 0.094 |
| CI-941 | — | n.d. | n.d. | 0.053 | 44.5 |
| doxorubicin | — | n.d. | n.d. | 0.58 | 53.8 |
| mitoxantrone | — | n.d. | n.d. | 0.024 | 0.67 | n.d. = not determined
IC$_{50}$ is the concentration of the drug which causes a 50% inhibition of the tumor cells growth
CYTOTOXICITY ON LOVO AND LOVO/DX WAS DETERMINED BY MTT ASSAY FOLLOWING 1 HOUR OF DRUG EXPOSURE

TABLE III

| Structure | Example | IC$_{50}$ ($\mu$g/ml) | | | |
| --- | --- | --- | --- | --- | --- |
| | | L1210 | S180 | LoVo | LoVo/Dx |
| [structure with NEt$_2$, NO$_2$] | ex. 11-cpd 1 | 0.00061 | 0.0031 | n.d. | n.d. |
| [structure with NMe$_2$, NO$_2$] | 4 | 0.00062 | 0.0032 | n.d. | n.d. |
| [structure with NMe$_2$, NO$_2$] | 3 | 0.05 | 0.14 | n.d. | n.d. |
| [structure with NEt$_2$, NO$_2$] | ex. 11-cpd 2 | 0.2 | 0.22 | n.d. | n.d |

TABLE III-continued

| | | IC$_{50}$ ($\mu$g/ml) | | | |
|---|---|---|---|---|---|
| Structure | Example | L1210 | S180 | LoVo | LoVo/Dx |
| 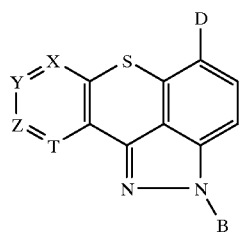 | 1 | 0.08 | 0.17 | n.d. | n.d. | n.d. = not determined
IC$_{50}$ is the concentration of the drug causes a 50% inhibition of the tumor cells growth
CYTOTOXICITY ON LOVO AND LOVO/DX WAS DETERMINED BY MTT ASSAY FOLLOWING 1 HOUR OF DRUG EXPOSURE

I claim:

1. A compound of formula (I):

(I)

wherein:
- one of X, Y, Z, or T is nitrogen (=N—) and the others are =CH—; D is selected from the group consisting of nitro or —NH—A, wherein A is selected in the group consisting of hydrogen, —CO—CH$_2$—NR$_2$R$_3$, C$_1$–C$_{10}$ alkyl; C$_2$–C$_{10}$ alkyl having one or two substituents selected from the group consisting of OR$_1$ and —NR$_2$R$_3$; C$_2$–C$_{10}$ alkyl interrupted by one or two oxygen atoms or by one —NR$_4$—group, and said C$_2$–C$_{10}$ alkyl is optionally substituted by one or two hydroxy (OH) or —NR$_2$R$_3$ groups;
- B is selected from the group consisting of C$_1$–C$_{10}$ alkyl; C$_2$–C$_{10}$ alkyl having one or two substituents selected from the group consisting of OR$_1$ and —NR$_2$R$_3$; and C$_2$–C$_{10}$ alkyl interrupted by one or two oxygen atoms or by one —NR$_4$—group, wherein said C$_2$–C$_{10}$ alkyl is optionally substituted by one or two hydroxy (OH) or —NR$_2$R$_3$ groups;
- R$_1$ is selected from the group consisting of hydrogen, C$_1$–C$_6$ alkyl, —S(O$_2$)R$_5$, and C$_2$–C$_6$ alkyl optionally substituted by —NR$_2$R$_3$;
- R$_2$ and R$_3$ may be the same or different and are selected from the group consisting of hydrogen, C$_1$–C$_{10}$ alkyl and C$_2$–C$_{10}$ alkyl substituted with one or two hydroxy (OH) groups; or R$_2$ and R$_3$ taken together with the nitrogen atom to which they are linked form a 5- or 6-member aromatic or non-aromatic heterocyclic ring which optionally contains a sulfur or oxygen atom or another nitrogen atom;
- R$_4$ is selected from the group consisting of hydrogen, C$_1$–C$_{10}$ alkyl, C$_2$–C$_{10}$ hydroxyalkyl, and C$_2$–C$_{10}$ alkyl substituted with —NR$_2$R$_3$;
- R$_5$ is selected from the group consisting of C$_1$–C$_{10}$ alkyl, phenyl, and phenylalkyl; as free bases and their salts with pharmaceutically acceptable acids.

2. The compound of claim 1 wherein C$_1$–C$_{10}$ alkyl is selected from the group consisting of methyl, ethyl, n-propyl, sec-propyl, n-butyl, sec-butyl, tert-butyl, n-pentyl, n-hexyl.

3. The compound of claim 1 wherein phenylalkyl is 4-methylphenyl.

4. The compound of claim 1 wherein the —NR$_2$R$_3$ substituent is selected from the group consisting of 1-imidazolyl, 4-hydroxy-1-imidazolyl, 2-imino-1(3H)-imidazolyl, 1-pyrrolyl, 1-tetrahydropyrrolyl, 1-pyrazolyl, 4-morpholinyl, 1-piperidinyl, 1-piperazinyl, 1-(4-methyl)piperazinyl, and 1-(4-benzyl)piperazinyl.

5. The compound of claim 1 selected from the group consisting of
(1) N,N-dimethyl-5-nitro-2H-pyrido[3',2':5,6]thiopyrano[4,3,2-cd]indazole-2-ethanamine;
(2) N'-[2-[2-(diethylamino)ethyl]-2H-pyrido[3',2':5,6]thiopyrano[4,3,2-cd]indazol-5-yl]-1,2-ethanediamine;
(3) N'-[2-[2-(methylamino)ethyl]-2H-pyrido[3',2':5,6]thiopyrano[4,3,2cd]indazol-5-yl]-1,2-ethanediamine;
(4) N'-[2-(2-aminoethyl]-2H-pyrido[3',2':5,6]thiopyrano[4,3,2-cd]indazol-5-yl]-1,2H-) ethanediamine;
(5) N'-[2-[2-(2-hydroxyethylamino)ethyl]-2H-pyrido[3',2':5,6]thiopyrano[4,3,2,-cd]indazol-5-yl]-1,2-ethanediamine;
(6) N'-[2-[2-(dimethylamino)ethyl]-2H-pyrido[3',2':5,6]thiopyrano[4,3,2-cd]indazol-5-yl]—N-methyl-1,2-ethanediamine,
(7) N'-[2-[2-(diethylamino)ethyl]-2H-pyrido[3',2':5,6]thiopyrano[4,3,2-cd]indazol-5-yl—N-methyl-1,2-ethanediamine;
(8) N'-[2-[2-(methylamino)ethyl]-2H-pyrido[3',2':5,6]thiopyrano[4,3,2-cd]indazol-5-yl]—N-methyl-1,2-ethanediamine;
(9) N'-[2-[2-aminoethyl]-2H-pyrido[3',2':5,6]thiopyrano[4,3,2-cd]indazol-methyl-1,2-ethanediamine;
(10) N'-[2-[2-(2-hydroxyethylamino)ethyl]-2H-pyrido[3',2':5,6]thiopyrano[4,3,2-cd]indazol-5-yl]—N-methyl-1,2-ethanediamine;
(11) N'-[2-[2-(dimethylamino)ethyl]-2H-pyrido3', 2':5,6]thiopyrano[4,3,2-cd]indazol-5-yl]—N-hydroxyethyl-1,2-ethanediamine;
(12) N'-[2-[2-(diethylamino)ethyl]-2H-pyrido[3',2':5,6]thiopyrano[4,3,2-cd ]indazol-5-yl]-N-hydroxyethyl-1,2-ethanediamine;

(13) N'-[2-[2-(methylamino)ethyl]-2H-pyrido[3',2':5,6]thiopyrano[4,3,2-cd]indazol-5-yl]-N-hydroxyethyl-1,2-ethanediamine;

(14) N'-[2-[2-aminoethyl]-2H-pyrido[3',2:5,6]thiopyrano[4,3,2-cd]indazol-5-yl]-N-hydroxyethyl-1,2-ethanediamine;

(15) N'-[2-[2-(2-hydroxyethylamino)ethyl]-2H-pyrido[3',2':5,6]thiopyrano[4,3,2-cd]indazol-5-yl]-N-hydroxyethyl-1,2-ethanediamine;

(16) N-[2-[2-(dimethylamino)ethyl]-2H-pyrido[3',2':5,6]thiopyrano[4,3,2-cd]indazol-5-yl]-2-aminoethanol;

(17) N-[2-[2-(diethylamino)ethyl]-2H-pyrido[3',2':5,6]thiopyrano[4,3,2-cd]indazol-5-yl]-2-aminoethanol;

(18) N-[2-[2-(methylamino)ethyl]-2H-pyrido[3',2':5,6]thiopyrano[4,3,2-cd]indazol-5-yl]-2-aminoethanol;

(19) N-[2-[2-aminoethyl]-2H-pyrido[3',2':5,6]thiopyrano[4,3,2-cd]indazol-5-yl]-2-aminoethanol;

(20) N-[2-[2-(2-hydroxyethylamino)ethyl]-2H-pyrido[3',2:5,6]thiopyrano[4,3,2-cd]indazol-5-yl]-2-aminoethanol;

(21) N'-[2-[2-(dimethylamino)ethyl]-2H-pyrido[4',3':5,6]thiopyrano(4,3,2-cd]indazol-5-yl]-N,N-dimethyl-1,2-ethanediamine;

(22) N'-[2-[2-(diethylamino)ethyl]-2H-pyrido[4',3':5,6]thiopyrano[4,3,2-cd]indazol-5-yl]-N,N-dimethyl-1,2-ethanediamine;

(23) N'-[2-[2-(methylamino)ethyl]-2H-pyrido[4',3':5,6]thiopyrano[4,3,2-cd]indazol-5-yl]-N,N-dimethyl-1,2-ethanediamine;

(24) N'-[2-[2-aminoethyl]-2H-pyrido[4',3':5,6]thiopyrano[4,3,2-cd]indazol-5-yl]-N,N-dimethyl-1,2-ethanediamine;

(25) N'-[2-[2-(2-hydroxyethylamino)ethyl]-2H-pyrido[4',3':5,6]thiopyrano(4,3,2-cd]indazol-5-yl]-N,N-dimethyl-1,2-ethanediamine;

(26) N'-12-[2-(dimethylamino)ethyl]-2H-pyrido[4,3':5,6]thiopyrano[4,3,2-cd]indazol-5-yl]-1,2-ethanediamine;

(27) N'-[2-[2-(diethylamino)ethyl]-2H-pyrido[4',3':5,6]thiopyrano[4,3,2-cd]indazol-5-yl]-1,2-ethanediamine;

(28) N'-[2-[2-(methylamino)ethyl]-2H-pyrido[4',3':5,6]thiopyrano[4,3,2-cd]indazol-5-yl]-1,2-ethanediamine;

(29) N'-[2-[2-aminoethyl]-2H-pyrido(4',3':5,6]thiopyrano[4,3,2-cd]indazol-5-yl]-1,2-ethanediamine;

(30) N'-[2-[2-(2-hydroxyethylamino)ethyl]-2H-pyrido[4',3':5,6]thiopyrano[4,3,2-cd]indazol-5-yl]-1,2-ethanediamine;

(31) N'-[2-[2-(dimethylamino)ethyl]-2H-pyrido[4',3':5,6]thiopyrano[4,3,2-cd]indazol-5-yl]-N-methyl-1,2-ethanediamine;

(32) N'-[2-[2-(diethylamino)ethyl]-2H-pyrido[4',3':5,6)thiopyrano[4,3,2cd]indazol-5-yl]-N-methyl-1,2-ethanediamine;

(33) N'-[2-[2-(methylamino)ethyl]-2H-pyrido[4',3':5,6]thiopyrano[4,3,2-5-yl]-N-methyl-1,2-ethanediamine;

(34) N'-[2-[2-aminoethyl]-2H-pyrido[4',3':5,6]thiopyrano[4,3,2-cd]indazol-5-yl]-N-methyl-1,2-ethanediamine;

(35) N'-[2-[2-(2-hydroxyethylamino)ethyl]-2H-pyrido[4',3':5,6]thiopyrano4,3,2-cd]indazol-5-yl]-N-methyl-1,2-ethanediamine;

(36) N'-[2-[2-(dimethylamino)ethyl]-2H-pyrido[4',3':5,6]thiopyrano[4,3,2-cd]indazol-5-yl]-N-hydroxyethyl-1,2-ethanediamine;

(37) N'-[2-[2-(diethylamino)ethyl]-2H-pyrido[4',3':5,6)thiopyrano[4,3,2-cd]indazol-5-yl]-N-hydroxyethyl-1,2-ethanediamine;

(38) N'-[2-[2-(methylamino)ethyl]-2H-pyrido[4',3':5,6]thiopyrano[4,3,2-cd]indazol -5-yl]-N-hydroxyethyl-1,2-ethanediamine;

(39) N'-[2-[2-aminoethyl]-2H-pyrido[4',3':5,6]thiopyrano(4,3,2-cd]indazol-5-yl-N-hydroxyethyl-1,2-ethanediamine;

(40) N'-12-[2-(2-hydroxyethylamino)ethyl]-2H-pyrido[4',3':5,6]thiopyrano[4,3,2-cd]indazol-5-yl]-N-hydroxyethyl-1,2-ethanediamine;

(41) N-[2-[2-(dimethylamino)ethyl]-2H-pyrido[4',3':5,6]thiopyrano[4,3,2-cd]indazol-5-yl]-2-aminoethanol;

(42) N-[2-[2-(diethylamino)ethyl]-2H-pyrido[4',3':5,6]thiopyrano[4,3,2-cd]indazol-5-yl]-2-aminoethanol;

(43) N-[2-[2-(methylamino)ethyl]-2H-pyrido[4',3':5,6]thiopyrano[4,3,2-cd]indazol-5-yl]-2-aminoethanol;

(44) N-[2-[2-aminoethyl]-2H-pyrido[4',3':5,6]thiopyrano[4,3,2-cd]indazol-5-yl]-2-aminoethanol;

(45) N-2-[2-(2-hydroxyethylamino)ethyl]-2H-pyrido[4',3':5,6]thiopyrano[4,3,2-cd]indazol-5-yl]-2-aminoethanol;

(46) N'-[2-[2-(dimethylamino)ethyl]-2H-pyrido[3',4':5,6]thiopyrano[4,3,2-cd]indazol-5-yl]-N,N-dimethyl-1,2-ethanediamine,

(47) N'-[2-[2-(diethylamino)ethyl]-2H-pyrido[3',4':5,6]thiopyrano[4,3,2-cd]indazol-5-yl]-N,N-dimethyl-1,2-ethanediamine;

(48) N'-[2-[2-(methylamino)ethyl]-2H-pyrido[3',4':5,6]thiopyrano[4,3,2-cd]indazol-5-yl]-N,N-dimethyl-1,2-ethanediamine;

(49) N'-[2-[2-aminoethyl-2H-pyrido[3',4':5,6]thiopyrano[4,3,2-cd]indazol-5-yl]-N,N-dimethyl-1,2-ethanediamine;

(50) N'-[2-[2-(2-hydroxyethylamino)ethyl]-2H-pyrido[3',4':5,6]thiopyrano[4,3,2-cd]indazol-5-yl]-N,N-dimethyl-1,2-ethanediamine;

(51) N'-[2-[2-(diethylamino)ethyl]-2H-pyrido[3',4':5,6]thiopyrano[4,3,2,-cd]indazol-5-yl]-1,2-ethanediamine;

(52) N'-[2-[2-(methylamino)ethyl]-2H-pyrido[3',4':5,6]thiopyrano[4,3,2-cd]indazol-5-yl]-1,2-ethanediamine;

(53) N'-[2-[2-aminoethyl]-2H-pyrido[3',4:5,6]thiopyrano[4,3,2-cd]indazol-5-yl]-1,2-ethanediamine;

(54) N'-[2-[2-(2-hydroxyethylamino)ethyl]-2H-pyrido[3',4':5,6]thiopyrano[4,3,2-cd]indazol-5-yl]-1,2-ethanediamine;

(55) N'-[2-[2-(dimethylamino)ethyl]-2H-pyrido[3',4':5,6]thiopyrano[4,3,2-cd]indazol-5-yl]-N-methyl-1,2-ethanediamine;

(56) N'-[2-[2-(diethylamino)ethyl]-2H-pyrido[3',4':5,6]thiopyrano[4,3,2-cd]indazol-5-yl]-N-methyl-1,2-ethanediamine;

(57) N'-[2-[2-(methylamino)ethyl]-2H-pyrido[3',4':5,6]thiopyrano[4,3,2-cd]indazol-5-yl]-N-methyl-1,2-ethanediamine;

(58) N'-[2-[2-aminoethyl]-2H-pyrido[3',4':5,6]thiopyrano[4,3,2-cd]indazol-5-yl]-N-methyl-1,2-ethanediamine;

(59) N'-(2-[2-(2-hydroxyethylamino)ethyl]-2H-pyrido[3',4':5,6]thiopyrano[4,3,2-cd]indazol-5-yl]-N-methyl-1,2-ethanediamine;

(60) N'-[2-[2-(dimethylamino)ethyl]-2H-pyrido[3',4':5,6]thiopyrano(4,3,2-cd]indazol-5-yl]-N-hydroxyethyl-1,2-ethanediamine;

(61) N'-[2-[2-(diethylamino)ethyl]-2H-pyrido[3',4':5,6]thiopyrano[4,3,2-cd]indazol-5-yl]-N-hydroxyethyl-1,2-ethanediamine;

(62) N'-[2-[2-(methylamino)ethyl]-2H-pyrido(3',4':5,6]thiopyrano[4,3,2-cd]indazol-5-yl]-N-hydroxyethyl-1,2-ethanediamine;

(63) N'-[2-[2-aminoethyl]-2H-pyrido[3',4':5,6]thiopyrano[4,3,2-cd]indazol-5-yl]-N-hydroxyethyl-1,2-ethanediamine;

(64) N'-[2-[2-(2-hydroxyethylamino)ethyl]-2H-pyrido[3',4':5,6]thiopyrano[4,3,2-cd]indazol-5-yl]-N-hydroxyethyl-1,2-ethanediamine;

(65) N-[2-[2-(dimethylamino)ethyl]-2H-pyrido[3',4':5,6]thiopyrano[4,3,2-cd]indazol-5-yl]-2-aminoethanol;

(66) N-[2-[2-(diethylamino)ethyl]-2H-pyrido[3',4':5,6]thiopyrano[4,3,2-cd]indazol-5-yl]-2-aminoethanol;
(67) N-[2-[2-(methylamino)ethyl]-2H-pyrido[3',4':5,6]thiopyrano[4,3,2-cd]indazol-5-yl]-2-aminoethanol;
(68) N-[2-[2-aminoethyl]-2H-pyrido[3',4':5,6]thiopyrano[4,3,2-cd]indazol-5-yl]-2-aminoethanol;
(69) N-[2-[2-(2-hydroxyethylamino)ethyl]-2H-pyrido[3',4':5,6]thiopyrano[4,3,2-cd]indazol-5-yl]-2-aminoethanol;
(70) N'-[2-[2-(dimethylamino)ethyl]-2H-pyrido[2',3':5,6]thiopyrano[4,3,2-cd]indazol-5-yl]-N,N-dimethyl-1,2-ethanediamine;
(71) N'-[2-[2-(diethylamino)ethyl]-2H-pyrido[2',3':5,6]thiopyrano[4,3,2-cd]indazol-5-yl]-N,N-dimethyl-1,2-ethanediamine;
(72) N'-[2-[2-(methylamino)ethyl]-2H-pyrido[2',3':5,6]thiopyrano[4,3,2-cd]indazol-5-yl]-N,N-dimethyl-1,2-ethanediamine;
(73) N'-[2-[2-aminoethyl]-2H-pyrido[2',3':5,6]thiopyrano[4,3,2-cd]indazol-5-yl]-N,N-dimethyl-1,2-ethanediamine;
(74) N'-[2-[2-(2-hydroxyethylamino)ethyl]-2H-pyrido[2',3':5,6]thiopyrano[4,3,2-cd]indazol-5-yl]-N,N-dimethyl-1,2-ethanediamine;
(75) N'-[2-[2-(dimethylamino)ethyl]-2H-pyrido[2',3':5,6]thiopyrano[4,3,2-cd]indazol-5-yl]-1,2-ethanediamine;
(76) N'-[2-[2-(diethylamino)ethyl]-2H-pyrido[2',3':5,6]thiopyrano[4,3,2-cd]indazol-5-yl]-1,2-ethanediamine;
(77) N'-[2-[2-(methylamino)ethyl]-2H-pyrido[2',3':5,6]thiopyrano[4,3,2-cd]indazol-5-yl]-1,2-ethanediamine;
(78) N'-[2-[2-aminoethyl]-2H-pyrido[2',3':5,6]thiopyrano[4,3,2-cd]indazol-5-yl]-1,2-ethanediamine;
(79) N'-[2-[2-(2-hydroxyethylamino)ethyl]-2H-pyrido[2',3':5,6]thiopyrano[4,3,2-cd]indazol-5-yl]-1,2-ethanediamine;
(80) N'-[2-[2-(dimethylamino)ethyl]-2H-pyrido[2',3':5,6]thiopyrano[4,3,2-cd]indazol-5-yl]-N-methyl-1,2-ethanediamine;
(81) N'-[2-[2-(diethylamino)ethyl-2H-pyrido[2',3':5,6]thiopyrano[4,3,2-cd]indazol-5-yl]-N-methyl-1,2-ethanediamine;
(82) N'-[2-[2-(methylamino)ethyl]-2H-pyrido[2',3':5,6]thiopyrano[4,3,2-cd]indazol-5-yl]-N-methyl-1,2-ethanediamine;
(83) N'-[2-[2-aminoethyl]-2H-pyrido[2',3':5,6]thiopyrano[4,3,2-cd]indazol-5-yl]-N-methyl-1,2-ethanediamine;
(84) N'-[2-[2-(2-hydroxyethylamino)ethyl]-2H-pyrido[2',3':5,6]thiopyrano[4,3,2-cd]indazol-5-yl]-N-methyl-1,2-ethanediamine;
(85) N'-[2-[2-(dimethylamino)ethyl]-2H-pyrido[2',3':5,6]thiopyrano[4,3,2-cd]indazol-5-yl]-N-hydroxyethyl-1,2-ethanediamine;
(86) N'-[2-[2-(diethylamino)ethyl]-2H-pyrido[2',3':5,6]thiopyrano[4,3,2-cd]indazol-5-yl]-N-hydroxyethyl-1,2-ethanediamine;
(87) N'-[2-[2-(methylamino)ethyl]-2H-pyrido[2',3':5,6]thiopyrano[4,3,2-cd]indazol-5-yl]-N-hydroxyethyl-1,2-ethanediamine;
(88) N'-[2-[2-aminoethyl]-2H-pyrido[2',3':5,6]thiopyrano[4,3,2-cd]indazol-5-yl]-N-hydroxyethyl-1,2-ethanediamine;
(89) N'-[2-[2-(2-hydroxyethylamino)ethyl]-2H-pyrido[2',3':5,6]thiopyrano[4,3,2-cd]indazol-5-yl]-N-hydroxyethyl-1,2-ethanediamine;
(90) N-[2-[2-(dimethylamino)ethyl]-2H-pyrido[2',3':5,6]thiopyrano[4,3,2-cd]indazol-5-yl]-2-aminoethanol;
(91) N-[2-[2-(diethylamino)ethyl]-2H-pyrido[2',3':5,6]thiopyrano[4,3,2-cd]indazol-5-yl]-2-aminoethanol;
(92) N-[2-[2-(methylamino)ethyl]-2H-pyrido[2',3':5,6]thiopyrano[4,3,2-cd]indazol-5-yl]-2-aminoethanol;
(93) N-[2-[2-aminoethyl]-2H-pyrido[2',3':5,6]thiopyrano[4,3,2-cd]indazol-5-yl]-2-aminoethanol;
(94) N-[2-[2-(2-hydroxyethylamino)ethyl]-2H-pyrido[2',3':5,6]thiopyrano[4,3,2-cd]indazol-5-yl]-2-aminoethanol.

6. The compound of claim 1 selected from the group consisting of:
(1) N'-[2-(2-dimethylamino)ethyl]-5-(2'-amino-acetylamino)-2H-pyrido[3',2':5,6]thiopyrano[4,3,2-cd]indazole,
(2) N'-[2-(2-dimethylamino)ethyl]-5-(2'-amino-acetylamino)-2H-pyrido[3',4':5,6]thiopyrano[4,3,2-cd]indazole;
(3) N'-[2-(2-dimethylamino)ethyl]-5-(2'-amino-acetylamino)-2H-pyrido[4',3':5,6]thiopyrano[4,3,2-cd]indazole;
(4) N'-[2-(2-dimethylamino)ethyl]-5-(2'-amino-acetylamino)-2H-pyrido[2',3:5,6]thiopyrano[4,3,2-cd]indazole;
(5) N'-[2-(2-diethylamino)ethyl]-5-(2'-amino-acetylamino)-2H-pyrido[3',2':5,6]thiopyrano[4,3,2-cd]indazole;
(6) N'-[2-(2-diethylamino)ethyl]-5-(2'-amino-acetylamino)-2H-pyrido[3',4':5,6]thiopyrano[4,3,2-cd]indazole;
(7) N'-[2-(2-diethylamino)ethyl]-5-(2'-amino-acetylamino)-2H-pyrido[4',3':5,6]thiopyrano[4,3,2-cd]indazole;
(8) N'-[2-(2-diethylamino)ethyl]-5-(2'-amino-acetylamino)-2H-pyrido[2',3':5,6]thiopyrano[4,3,2-cd]indazole;
(9) N'-[2-(2-methylamino)ethyl]-5-(2'-amino-acetylamino)-2H-pyrido[3',2':5,6]thiopyrano[4,3,2-cd]indazole;
(10) N'-[2-(2-methylamino)ethyl]-5-(2'-amino-acetylamino)-2H-pyrido[3',4':5,6]thiopyrano[4,3,2-cd]indazole;
(11) N'-[2-(2-methylamino)ethyl]-5-(2'-amino-acetylamino)-2H-pyrido[4',3':5,6]thiopyrano[4,3,2-cd]indazole;
(12) N'-[2-(2-methylamino)ethyl]-5-(2'-amino-acetylamino)-2H-pyrido[2',3':5,6]thiopyrano[4,3,2-cd]indazole;
(13) N'-[2-aminoethyl]-5-(2'-amino-acetylamino)-2H-pyrido[3',2:5,6]thiopyrano[4,3,2-cd]indazole;
(14) N'-[2-aminoethyl]-5-(2'-amino-acetylamino)-2H-pyrido[3',4':5,6]thiopyrano[4,3,2-cd]indazole;
(15) N'-[2-aminoethyl]-5-(2'-amino-acetylamino)-2H-pyrido[4',3':5,6]thiopyrano[4,3,2-cd]indazole;
(16) N'-[2-aminoethyl]-5-(2'-amino-acetylamino)-2H-pyrido[2',3':5,6]thiopyrano[4,3,2-cd]indazole;
(17) N'-[2-(2-hydroxyethylamino)ethyl]-5-(2'-amino-acetylamino)-2H-pyrido[3',2':5,6]thiopyrano[4,3,2-cd]indazole;
(18) N'-[2-(2-hydroxyethylamino)ethyl]-5-(2'-amino-acetylamino)-2H-pyrido[3',4':5,6 thiopyrano[4,3,2-cd]indazole;
(19) N'-[2-(2-hydroxyethylamino)ethyl]-5-(2'-amino-acetylamino)-2H-pyrido[4',3':5,6]thiopyrano[4,3,2-cd]indazole;
(20) N'-[2-(2-hydroxyethylamino)ethyl]-5-(2'-amino-acetylamino)-2H-pyrido[2',3':5,6]thiopyrano[4,3,2-cd]indazole.

7. The compound of claim 1 selected from the group consisting of:
(1) N,N-diethyl-5-nitro-2H-pyrido[3',4':5,6]thiopyrano[4,3,2-cd]indazole-2-ethanamine,
(2) N,N-diethyl-5-nitro-2H-pyrido[3',2':5,6]thiopyrano[4,3,2-cd]indazole-2-ethanamine;
(3) N,N-dimethyl-5-nitro-2H-pyrido[4',3':5,6]thiopyrano[4,3,2-cd]indazole-2-ethanamine;
(4) N,N-diethyl-5-nitro-2H-pyrido[4',3':5,6]thiopyrano[4,3,2-cd]indazole-2-ethanamine;

(5) N,N-dimethyl-5-nitro-2H-pyrido[2',3':5,6]thiopyrano[4,3,2-cd]indazole-2-ethanamine;
(6) N,N-diethyl-5-nitro-2H-pyrido[2',3':5,6]thiopyrano[4,3,2-cd]indazole-2-ethanamine;
(7) N-methyl-5-nitro-2H-pyrido[3',4':5,6]thiopyrano[4,3,2-cd]indazole-2-ethanamine;
(8) N-methyl-5-nitro-2H-pyrido[3',2':5,6]thiopyrano[4,3,2-cd]indazole-2-ethanamine;
(9) N-methyl-5-nitro-2H-pyrido[4',3':5,6]thiopyrano[4,3,2-cd]indazole-2-ethanamine;
(10) N-methyl-5-nitro-2H-pyrido[2',3':5,6]thiopyrano[4,3,2-cd]indazole-2-ethanamine;
(11) 5-nitro-2H-pyrido[3',4':5,6]thiopyrano[4,3,2-cd]indazole-2-ethanamine;
(12) 5-nitro-2H-pyrido[3',2':5,6]thiopyrano[4,3,2-cd]indazole-2-ethanamine;
(13) 5-nitro-2H-pyrido[4',3':5,6]thiopyrano[4,3,2-cd]indazole-2-ethanamine;
(14) 5-nitro-2H-pyrido[2',3':5,6]thiopyrano[4,3,2-cd]indazole-2-ethanamine;
(15) N-hydroxyethyl-5-nitro-2H-pyrido[3',4':5,6]thiopyrano[4,3,2-cd]indazole-2-ethanamine;
(16) N-hydroxyethyl-5-nitro-2H-pyrido[3',2':5,6]thiopyrano[4,3,2-cd]indazole-2-ethanamine;
(17) N-hydroxyethyl-5-nitro-2H-pyrido[4',3':5,6]thiopyrano[4,3,2-cd]indazole-2-ethanamine;
(18) N-hydroxyethyl-5-nitro-2H-pyrido[2',3':5,6]thiopyrano[4,3,2-cd]indazole-2-ethanamine.

8. The compound of claim 1 selected from the group consisting of:
(1) N,N-diethyl-5-amino-2H-pyrido[3',4':5,6]thiopyrano[4,3,2-cd]indazole-2-ethanamine,
(2) N,N-diethyl-5-amino-2H-pyrido[3',2':5,6]thiopyrano[4,3,2-cd]indazole-2-ethanamine;
(3) N,N-dimethyl-5-amino-2H-pyrido[4',3':5,6]thiopyrano[4,3,2-cd]indazole-2-ethanamine;
(4) N,N-diethyl-5-amino-2H-pyrido[4',3':5,6]thiopyrano[4,3,2-cd]indazole-2-ethanamine;
(5) N,N-dimethyl-5-amino-2H-pyrido[2',3':5,6]thiopyrano[4,3,2-cd]indazole-2-ethanamine;
(6) N,N-diethyl-5-amino-2H-pyrido[2',3':5,6]thiopyrano[4,3,2-cd]indazole-2-ethanamine;
(7) N-methyl-5-amino-2H-pyrido[3',4':5,6]thiopyrano[4,3,2-cd]indazole-2-ethanamine;
(8) N-methyl-5-amino-2H-pyrido[3',2':5,6]thiopyrano[4,3,2-cd]indazole-2-ethanamine;
(9) N-methyl-5-amino-2H-pyrido[4',3':5,6]thiopyrano[4,3,2-cd]indazole-2-ethanamine;
(10) N-methyl-5-amino-2H-pyrido[2',3':5,6]thiopyrano[4,3,2-cd]indazole-2-ethanamine;
(11) 5-amino-2H-pyrido[3',4':5,6]thiopyrano[4,3,2-cd]indazole-2-ethanamine;
(12) 5-amino-2H-pyrido[3',2':5,6]thiopyrano[4,3,2-cd]indazole-2-ethanamine;
(13) 5-amino-2H-pyrido[4',3':5,6]thiopyrano[4,3,2-cd]indazole-2-ethanamine;
(14) 5-amino-2H-pyrido[2',3':5,6]thiopyrano[4,3,2-cd]indazole-2-ethanamine;
(15) N-hydroxyethyl-5-amino-2H-pyrido[3',4':5,6]thiopyrano[4,3,2-cd]indazole-2-ethanamine;
(16) N-hydroxyethyl-5-amino-2H-pyrido[3',2':5,6]thiopyrano[4,3,2-cd]indazole-2-ethanamine;
(17) N-hydroxyethyl-5-amino-2H-pyrido[4',3':5,6]thiopyrano[4,3,2-cd]indazole-2-ethanamine;
(18) N-hydroxyethyl-5-amino-2H-pyrido[2',3':5,6]thiopyrano[4,3,2-cd]indazole-2-ethanamine.

9. A pharmaceuticals composition comprising an effective amount of the compound of claim 1 and a pharmaceutically acceptable excipient.

10. A method of treating a tumor in a patient in need of such treatment comprising administering an anti-tumor effective amount of the compound of claim 1 to the patient.

11. A method of treating a tumor in a patient in need of such treatment comprising administering an anti-tumor effective amount of the compound of claim 5 to the patient.

12. A method of treating a tumor in a patient in need of such treatment comprising administering an anti-tumor effective amount of the compound of claim 8 to the patient.

13. The method of claim 10, wherein the tumor is sarcoma, leukemia or colon adenocarcinoma.

14. The method of claim 11, wherein the tumor is sarcoma, leukemia or colon adenocarcinoma.

15. The method of claim 14, wherein the tumor is sarcoma, leukemia or colon adenocarcinoma.

16. A method of making a compound of formula (I):

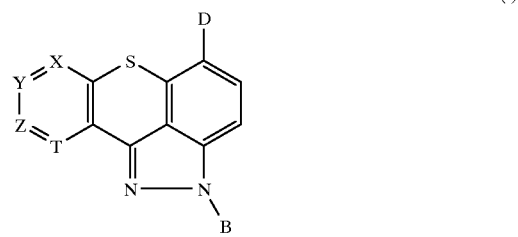

wherein:

one of X, Y, Z or T is a nitrogen atom and the others are =CH—;

D is nitro;

B is selected from the group consisting of $C_1$–$C_{10}$ alkyl; $C_2$–$C_{10}$ alkyl having one or two substituents selected from the group consisting of —$OR_1$ and —$NR_2R_3$; and $C_2$–$C_{10}$ alkyl interrupted by one or two oxygen atoms or by one —$NR_4$— group, wherein said $C_2$–$C_{10}$ alkyl is optionally substituted by one or two hydroxy or —$NR_2R_3$ groups, which one or two hydroxy or —$NR_2R_3$ groups are optionally protected by suitable protective group(s);

$R_1$ is selected from the group consisting of hydrogen, $C_1$–$C_6$ alkyl, —$S(O_2)R_5$, and $C_2$–$C_6$ alkyl optionally substituted by —$NR_2R_3$;

$R_2$ and $R_3$ may be the same or different and are selected from the group consisting of hydrogen, $C_1$–$C_{10}$ alkyl, and $C_2$–$C_{10}$ alkyl substituted with one or two hydroxy groups; or $R_2$ and $R_3$ taken together with the nitrogen atom to which they are linked form a 5- or 6-member aromatic or non-aromatic heterocyclic ring which optionally contains a sulfur or oxygen atom or another nitrogen atom;

$R_4$ is selected from the group consisting of hydrogen, $C_1$–$C_{10}$ alkyl, $C_2$–$C_{10}$ hydroxyalkyl, and $C_2$–$C_{10}$ alkyl substituted with —$NR_2R_3$; and $R_5$ is selected from the group consisting of $C_1$–$C_{10}$ alkyl, phenyl, and phenylakyl; said method comprising the following steps a) reacting a compound of formula (III):

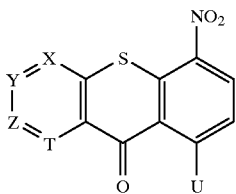

(III)

wherein X, Y, Z and T are as defined above and U is F or Cl, with a hydrazine of formula (IV):

H₂N—NH—B     (IV)

wherein B is as define above, to give a compound of formula (II):

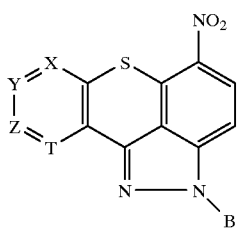

(II)

17. The method of claim 16, further comprising
a) reducing the nitro group of the compound of formula (II) to give the compound of formula (IIa):

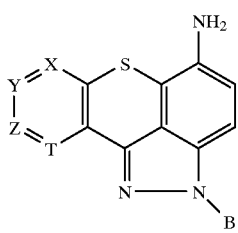

(IIa)

and thereafter
b) if the protective group(s) are present in B, removing the protective group(s); to obtain a compound of formula (I), wherein D is —NH—A and A is hydrogen.

18. The method of claim 17, further comprising
a) condensing the —NH—A group of the product of the method of claim 17 with a reactant of formula (V):

L—A'     (V)

wherein A' is selected from the group consisting of $C_1$–$C_{10}$ alkyl; $C_2$–$C_{10}$ alkyl having one or two substituents selected from the group consisting of —$OR_1$ and —$NR_2R_3$; $C_2$–$C_{10}$ alkyl interrupted by one or two oxygen atoms or by one —$NR_4$— group, and said $C_2$–$C_{10}$ alkyl is optionally substituted by one or two hydroxy or —$NR_2R_3$ groups, which one or two hydroxy or —$NR_2R_3$ groups are optionally protected by suitable protective group(s);
L is a chlorine, bromine or iodine atom or a —O-Tosyl group; and thereafter
b) if the protective group(s) is present in A' and/or B, removing the protective group(s);
to obtain a compound of formula (I), wherein D is —NH—A and A is selected from the group consisting of $C_1$–$C_{10}$ alkyl; $C_2$–$C_{10}$ alkyl having one or two substituents selected from the group consisting of —$OR_1$ and —$NR_2R_3$; $C_2$–$C_{10}$ alkyl interrupted by one or two oxygen atoms or by one —$NR_4$— group, and said $C_2$–$C_{10}$ alkyl is optionally substituted by one or two hydroxy or —$NR_2R_3$ groups.

19. The method of claim 17, further comprising
a) condensing the —NH—A group of the product of claim 17 with a reactant of formula (V"):

L'—CO—A"     (V")

wherein A" is
(i) $C_1$–$C_9$ alkyl;
(ii) $C_1$–$C_9$ alkyl having one or two substituents selected from the group consisting of $OR_1$ and —$NR_2R_3$, wherein $R_1$, $R_2$ and $R_3$ are as defined above; or
(iii) $C_1$–$C_9$ alkyl interrupted by one or two oxygen atoms or by one —$NR_4$— group, wherein said $C_1$–$C_9$ alkyl is optionally substituted by one or two hydroxy or —$NR_2R_3$ groups, which one or two hydroxy or —$NR_2R_3$ groups are optionally protected by suitable protective group(s), wherein $R_4$ is as defined above; and
L' is a chlorine, bromine or iodine atom, hydroxy group or another suitable leaving group; and thereafter
b) if the protective group(s) is present in A" and/or B, removing the protective group(s);
to obtain a compound of formula (I), wherein D is —NH—A and A is —CO—$CH_2$—$NR_2R_3$.

* * * * *